United States Patent
Ganz et al.

(10) Patent No.: US 8,038,940 B2
(45) Date of Patent: Oct. 18, 2011

(54) AUTOMATED MACHINE FOR TRANSFERRING SOLUTION FROM A SOURCE MICROWELL PLATE TO A DESTINATION MICROWELL PLATE

(75) Inventors: Brian L. Ganz, Carlsbad, CA (US); Nicholas Pratte, Encondido, CA (US); Richard Roberts, Valley Center, CA (US); David Jewell, San Diego, CA (US)

(73) Assignee: Lets Go Robotics, Inc., Carlsbad, CA (US)

( * ) Notice: Subject to any disclaimer, the term of this patent is extended or adjusted under 35 U.S.C. 154(b) by 453 days.

(21) Appl. No.: 12/359,306

(22) Filed: Jan. 24, 2009

(65) Prior Publication Data

US 2009/0235764 A1  Sep. 24, 2009

Related U.S. Application Data

(60) Provisional application No. 61/023,766, filed on Jan. 25, 2008.

(51) Int. Cl.
*G01N 27/00* (2006.01)
*B01L 3/02* (2006.01)
(52) U.S. Cl. .......................... 422/64; 422/510
(58) Field of Classification Search .................... 422/63, 422/64, 100, 502, 507, 510; 436/43
See application file for complete search history.

(56) References Cited

U.S. PATENT DOCUMENTS

| 4,681,741 A * | 7/1987 | Hanaway | 422/509 |
| 6,325,114 B1 * | 12/2001 | Bevirt et al. | 141/130 |
| 6,582,929 B2 * | 6/2003 | Dunfee et al. | 435/32 |

* cited by examiner

*Primary Examiner* — Hezron E Williams
*Assistant Examiner* — Nathaniel Kolb
(74) *Attorney, Agent, or Firm* — John R. Ross; John R. Ross, III

(57) ABSTRACT

An automated machine for transferring solution from a source microwell plate to a destination microwell plate. A plurality of pins is used for transferring the solution. The pins are attached to pin assemblies. The pin assemblies are attached to the circumference of a circular dial that is rotatably connected to the automated machine. The circular dial rotates the pins form a solution removal position to a solution transfer position and then to a pin cleaning position. Solution is removed from individual wells at the solution removal position and the solution is transferred to individual wells at the solution transfer position. The pins are cleaned at the pin cleaning position. A computer is programmed to control the automated machine and the transfer of solution. In a preferred embodiment, the computer is programmed to: 1) execute a saved transfer list, 2) accept a customized input list from an operator, 3) execute the customized input list, and 4) save the customized input list for later execution. In a preferred embodiment, the automated machine is utilized for transferring variable volumes of solution from the source microwell plate to the destination microwell plate.

19 Claims, 30 Drawing Sheets

US 8,038,940 B2

AUTOMATED MACHINE FOR TRANSFERRING SOLUTION FROM A SOURCE MICROWELL PLATE TO A DESTINATION MICROWELL PLATE

The present invention relates to automated microwell plate handling machines, and in particular to automated machines for transferring solution from a source microwell plate to a destination microwell plate. This application claims the benefit of U.S. provisional application Ser. No. 61/023,766 filed Jan. 25, 2008.

BACKGROUND OF THE INVENTION

Microwell plates, also known as microplates, are a standard product and are regularly used in the laboratory. Microwell plates play a very important role in genomic research as well as other medical, chemical and biological pursuits. Microwell plates have greatly improved the sample handling capabilities of high throughput genomic research labs. However, their increased popularity and usage in the laboratory has often proved difficult for the hands of a technician. For example, just as tubes were being juggled by technicians 10 years ago, microwell plates are now also being juggled. In response, there has been an effort in recent years to construct automated machines to more effectively and efficiently handle microwell plates.

Transfer of Solution Between Microwell Plates

For research and experimentation, it is desirable to be able to effectively transfer solution from a source microwell plate to a destination microwell plate. There are many types of transfer modes that are utilized. For example, a technician may want to make an exact copy of a microwell plate so that each well of the source plate has been replicated in its corresponding well of the destination plate. Or, for example, a technician may want to customize the transfer pattern by "cherry picking" a unique well on the source plate to a selected unique well on the destination plate.

Microarrays and Macroarrays

In general there are two types of arrays, microarrays and macroarrays. An array type is determined by the size and density of the sample spots. For example, microarrays have spots of 100 microns or less in diameter on a glass support. In comparison, macroarrays usually have spots of 250-300 micrometers in diameter and are usually prepared on a nylon support.

Prior art machines for transferring solution from a source microwell plate to a destination microwell plate are cumbersome and expensive. What is needed is a better automated machine for transferring solution from a source microwell plate to a destination microwell plate.

SUMMARY OF THE INVENTION

The present invention provides an automated machine for transferring solution from a source microwell plate to a destination microwell plate. A plurality of pins is used for transferring the solution. The pins are attached to pin assemblies. The pin assemblies are attached to the circumference of a circular dial that is rotatably connected to the automated machine. The circular dial rotates the pins from a solution removal position to a solution transfer position and then to a pin cleaning position. Solution is removed from individual wells at the solution removal position and the solution is transferred to individual wells at the solution transfer position. The pins are cleaned at the pin cleaning position. A computer is programmed to control the automated machine and the transfer of solution. In a preferred embodiment, the computer is programmed to: 1) execute a saved transfer list, 2) accept a customized input list from an operator, 3) execute the customized input list, and 4) save the customized input list for later execution. In a preferred embodiment, the automated machine is utilized for transferring variable volumes of solution from the source microwell plate to the destination microwell plate.

DETAILED DESCRIPTION OF THE PREFERRED EMBODIMENTS

Operation of a Preferred Embodiment

Figure 1:
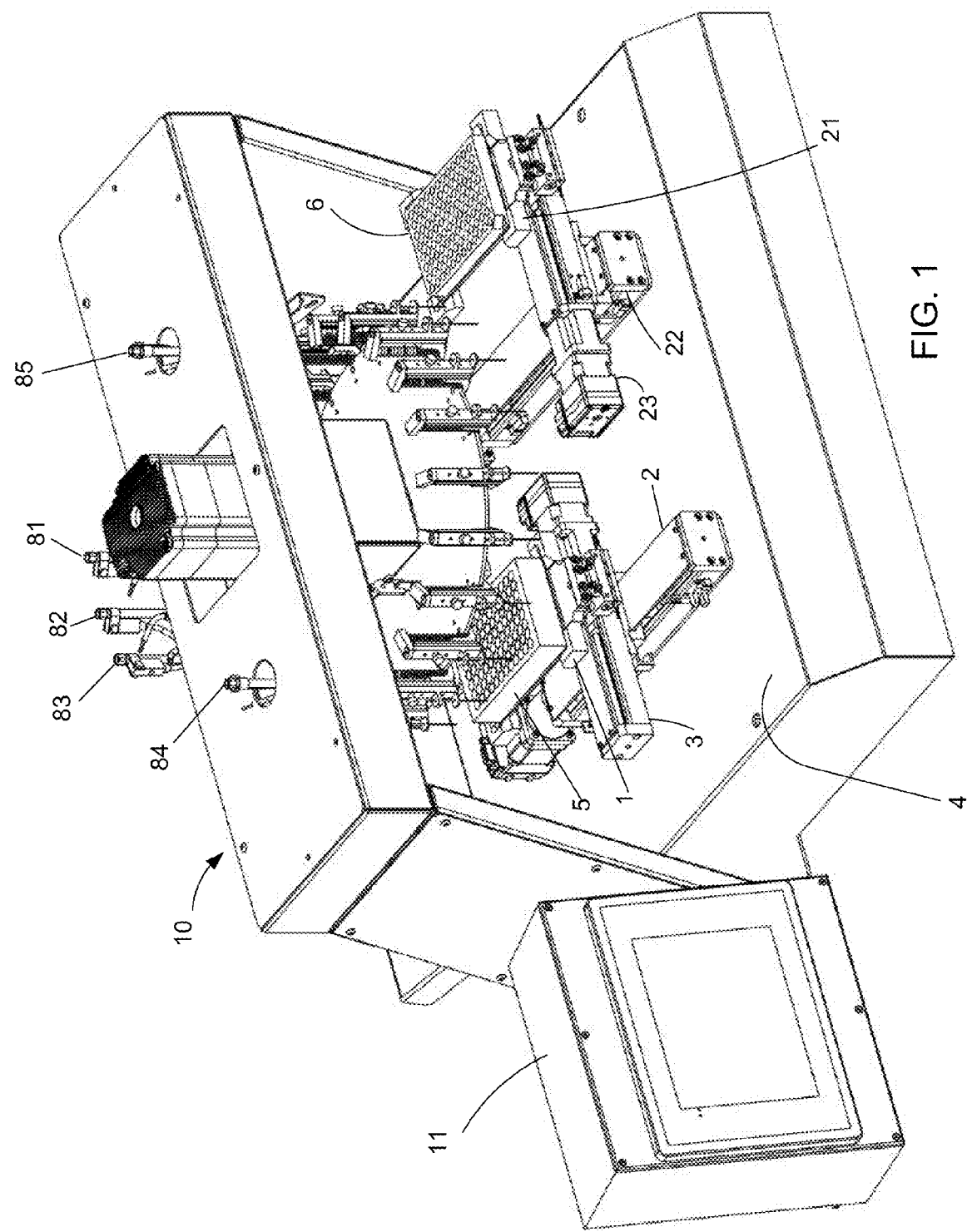
FIG. 1 shows a perspective view of a preferred embodiment of the present invention.

FIG. 1 shows a perspective view of a preferred embodiment of the present invention with source microwell plate 5 and destination microwell plate 6. Automated solution transfer machine 10 is controlled via computer 11.

An operation of a preferred embodiment of the present invention is seen by reference to FIGS. 2-31.

Loading the Source Plate

Figure 2:
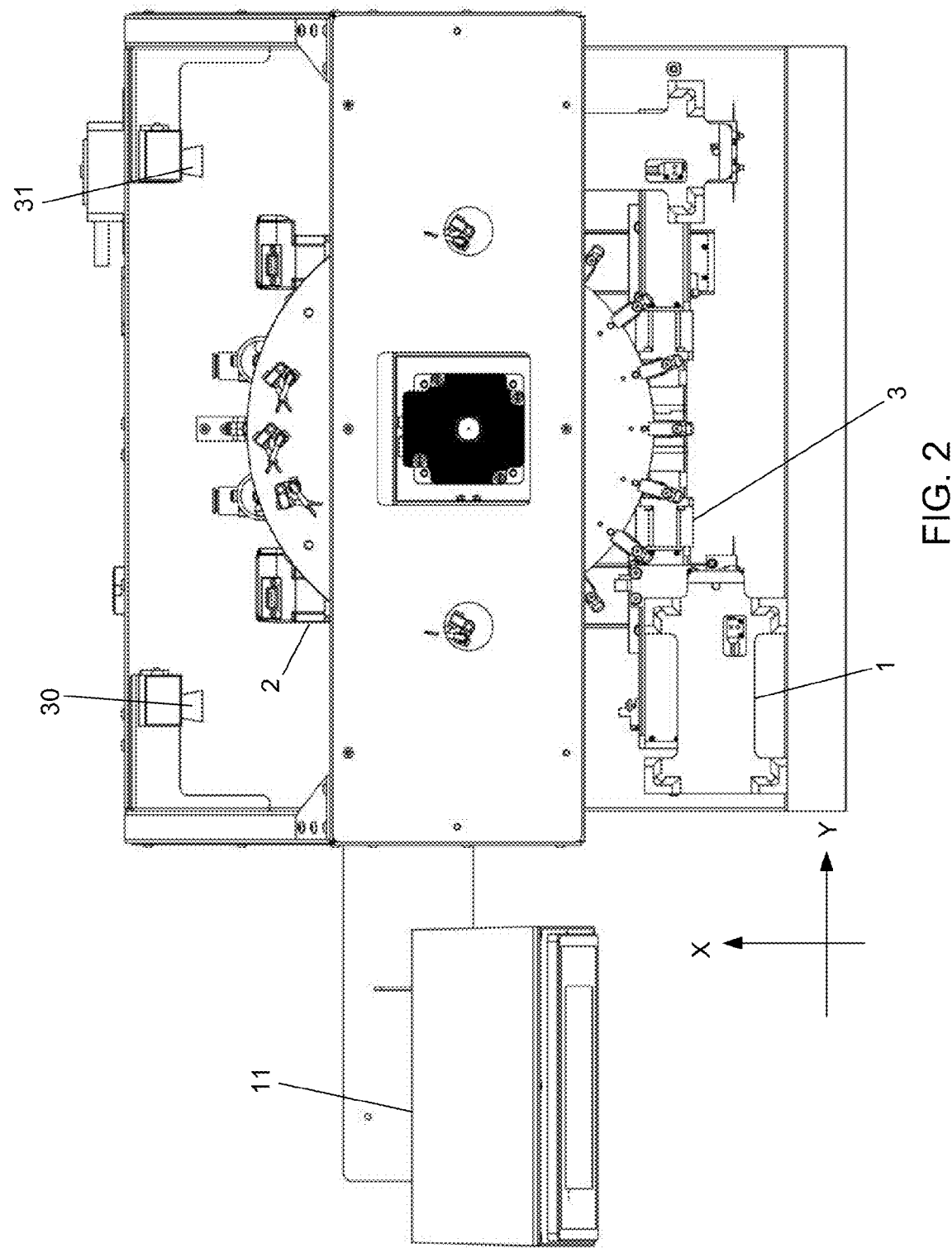
FIGS. 2-31 show sequence of operations of a preferred embodiment of the present invention.

In FIG. 2, source tray 1 has been positioned via computer 11 so that it is in proper position to receive a microwell plate. Linear actuator 2 is rigidly connected to platform 4 (see FIG. 1). Linear actuator 3 is mounted on top of linear actuator 2 and is horizontally moved by linear actuator 2. Source tray 1 is mounted to the top of linear actuator 3 and is moved horizontally by linear actuator 3. Linear actuators 2 and 3 act to move source tray 1 in the X and Y directions, respectively (see FIG. 2). Source tray 1 is also rotatably attached to the top of linear actuator 3.

Figure 3:
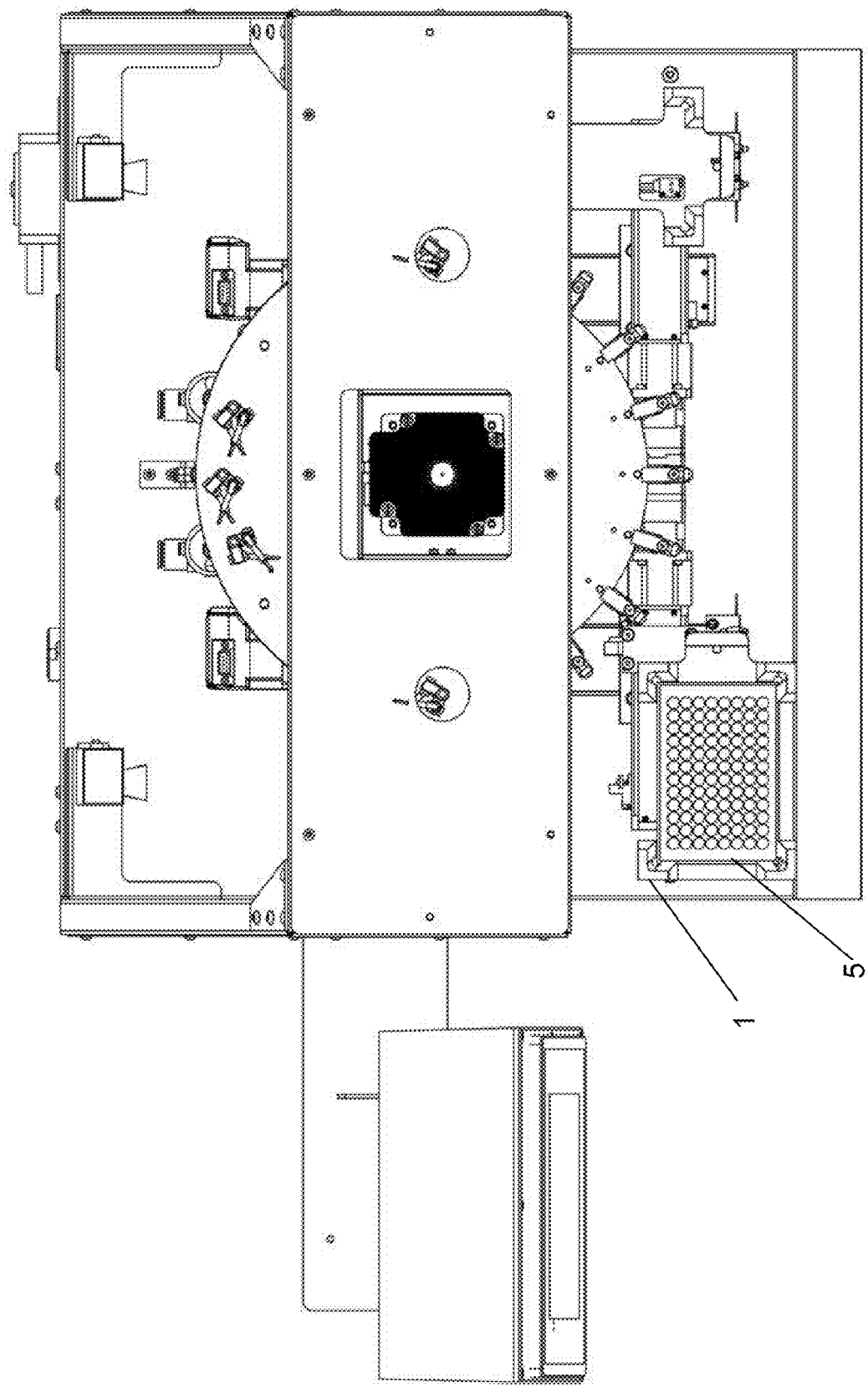

In FIG. 3, microwell plate 5 has been loaded onto source tray 1. In a preferred embodiment, an automated device has placed microwell plate 5 onto source tray 1.

Figure 4:
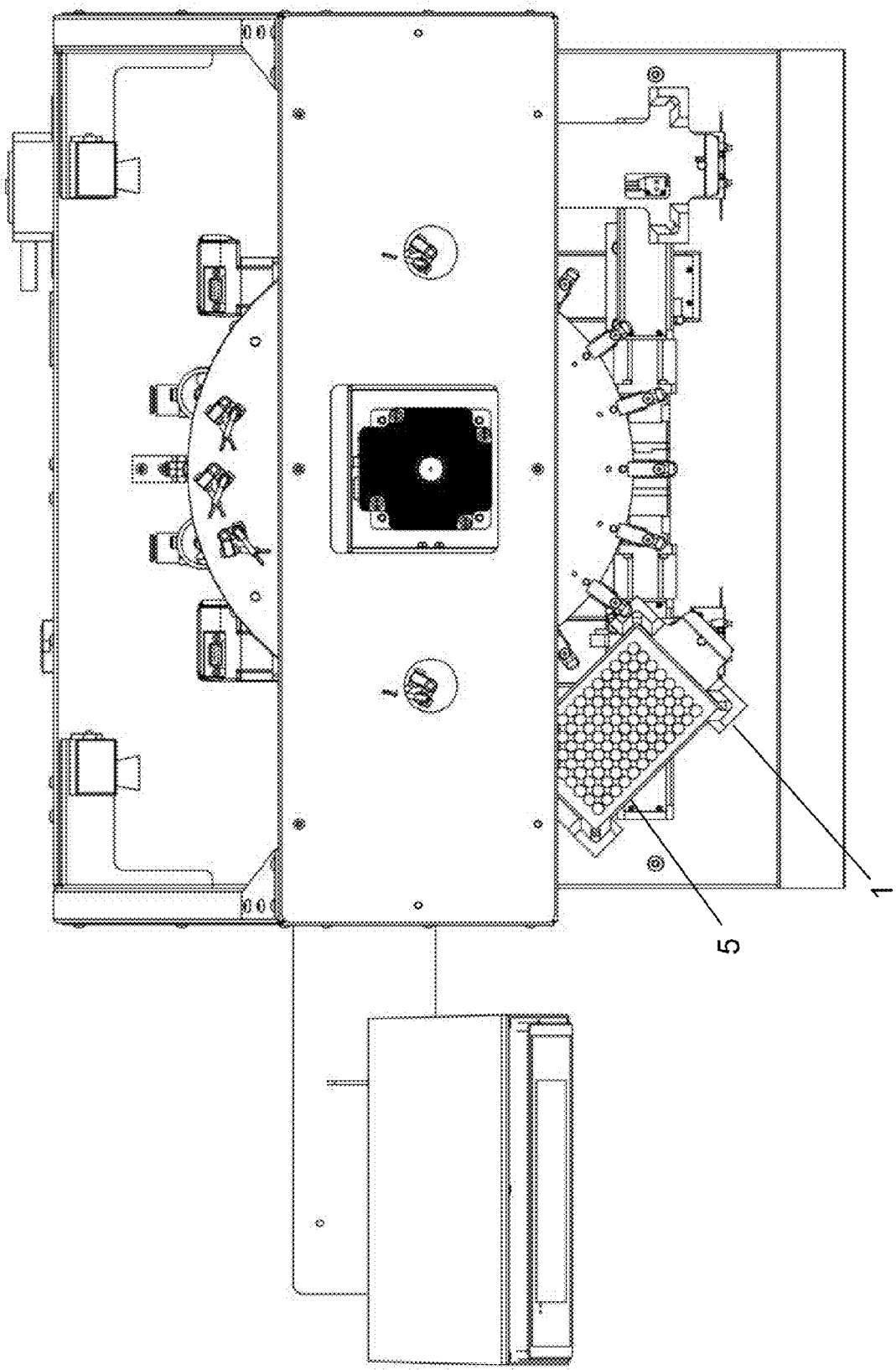

In FIG. 4, microwell plate 5 has been rotated clockwise approximately 45 degrees.

Figure 5:
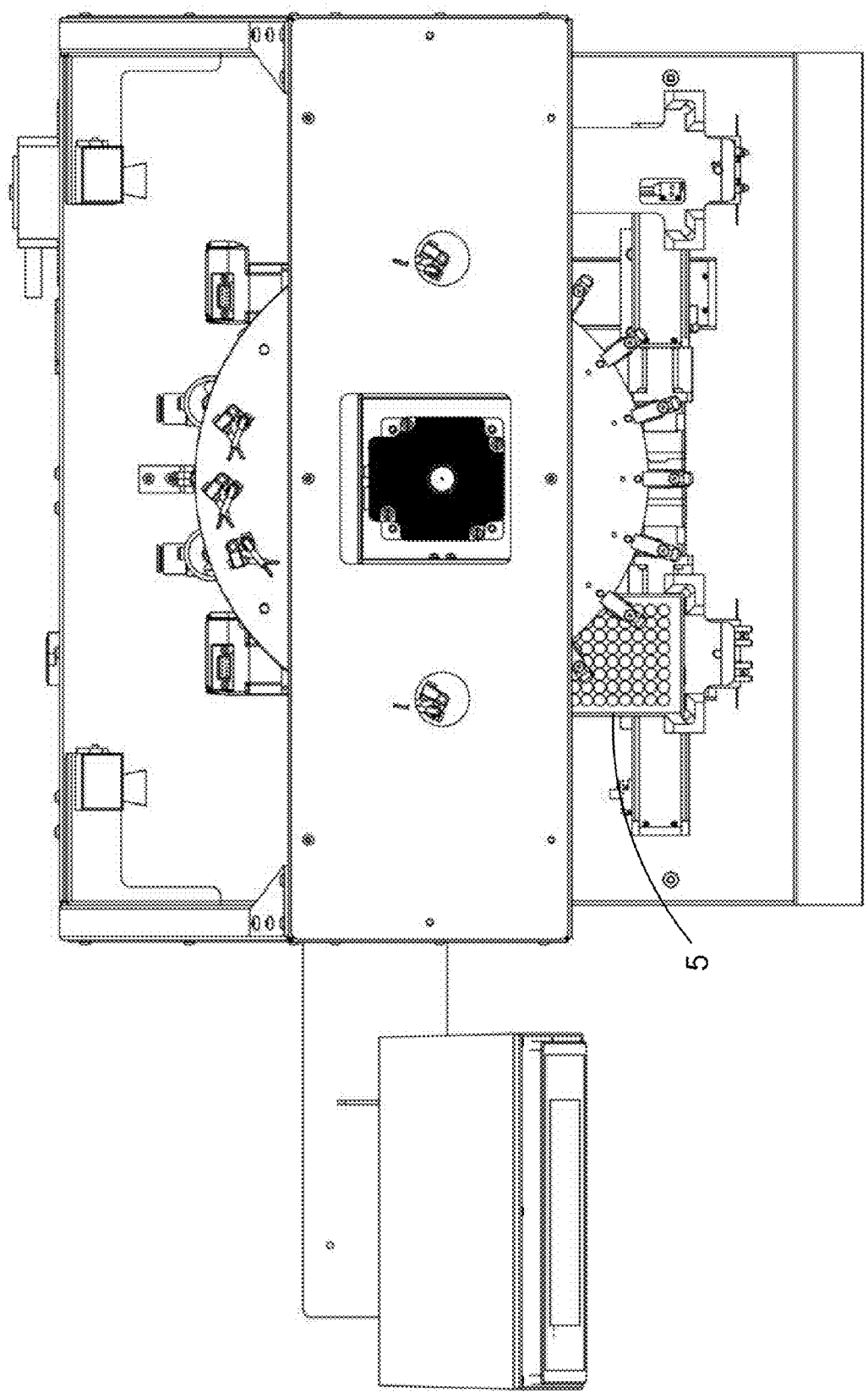

In FIG. 5, microwell plate 5 has been completely rotated 90 degrees clockwise from its position in FIG. 3.

Figure 6:
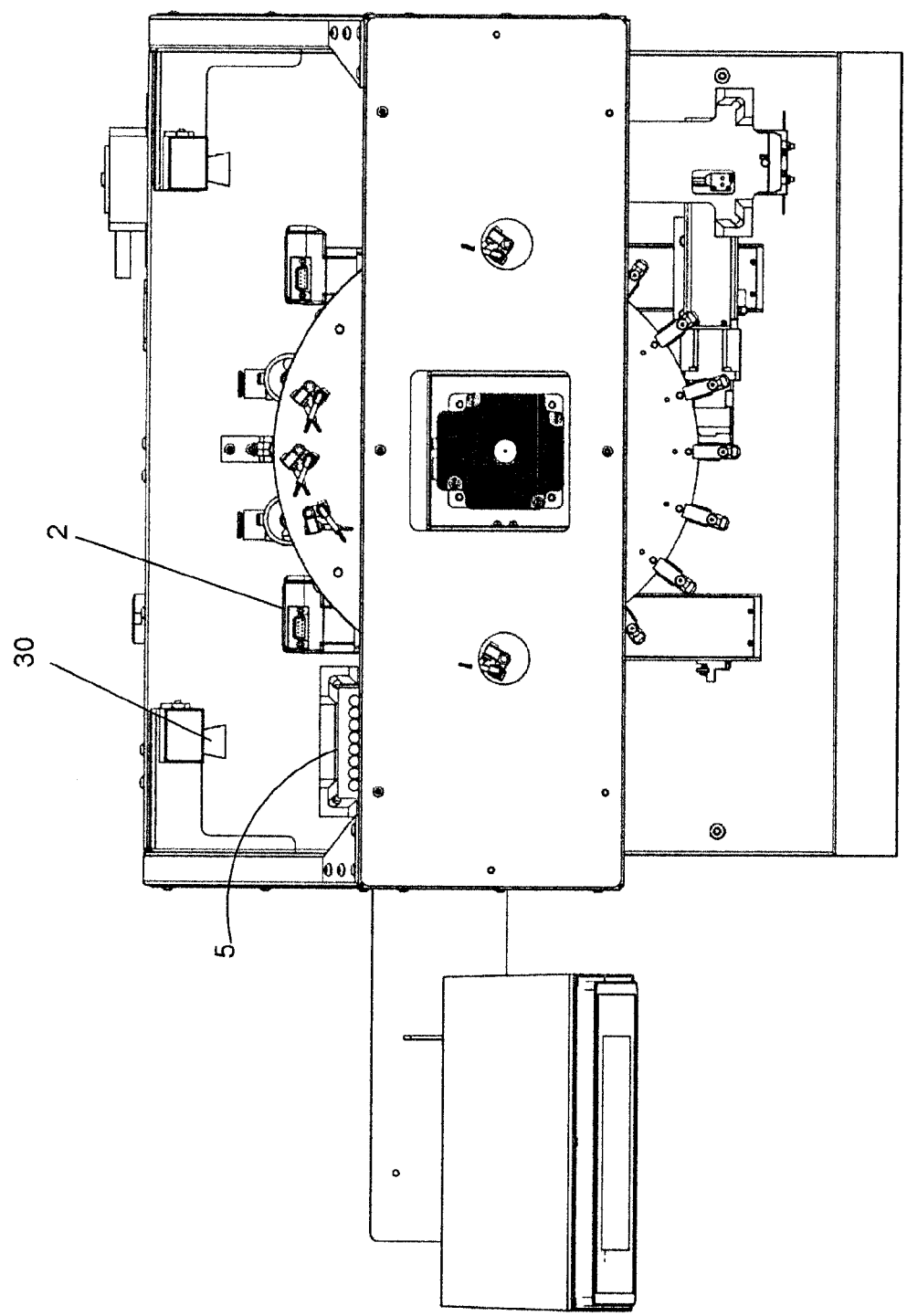

In FIG. 6, linear actuator 2 has moved microwell plate 5 towards barcode reader 30. Barcode reader 30 reads the barcode on microwell plate 5. This information is transferred to and recorded in computer 11.

Loading the Destination Plate

Figure 7:
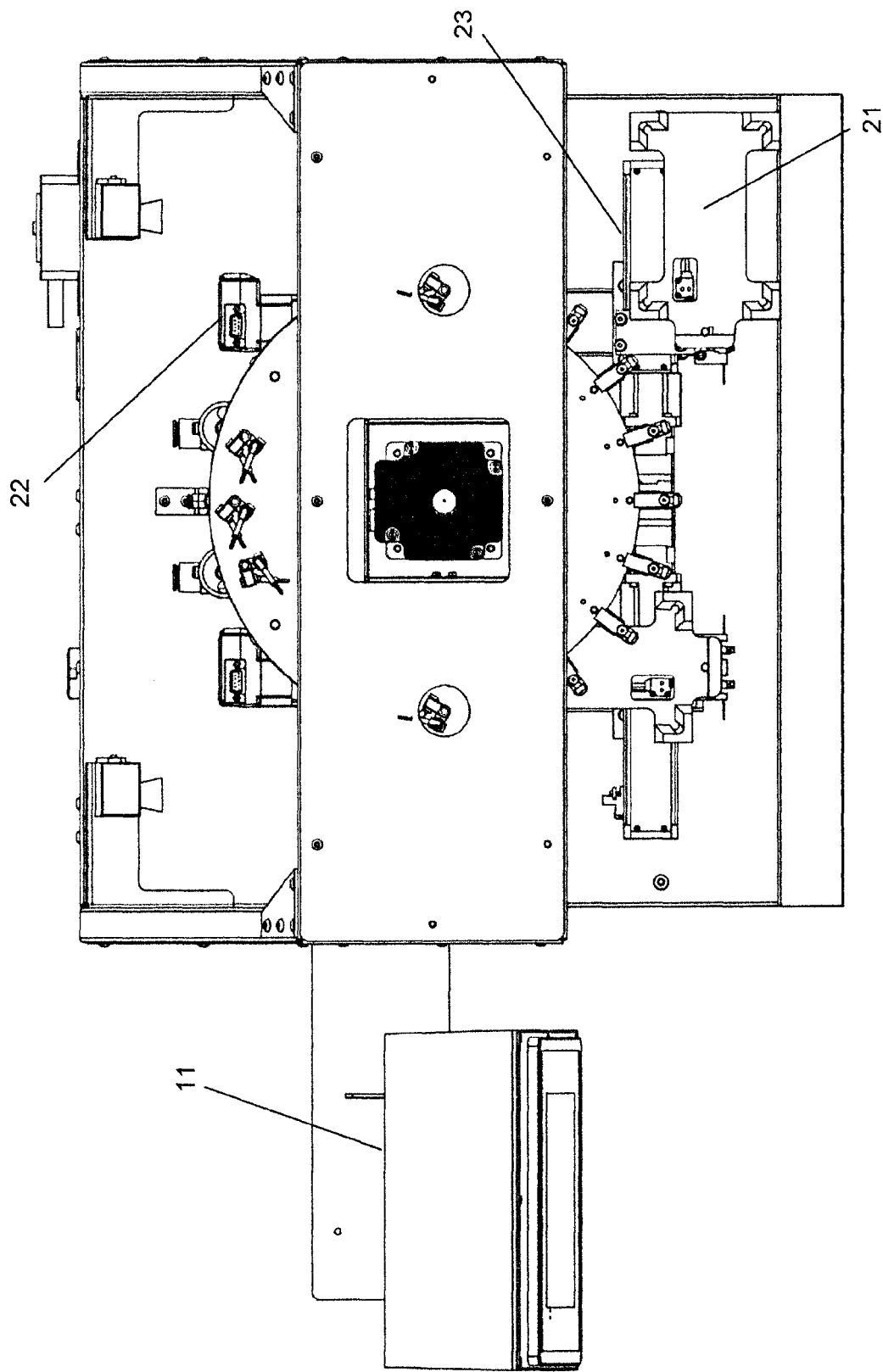

In FIG. 7, destination tray 21 has been positioned via computer 11 so that it is in proper position to receive a microwell plate. Linear actuator 22 is rigidly connected to platform 4 (see FIG. 1). Linear actuator 23 is mounted on top of linear actuator 22 and is horizontally moved by linear actuator 22. Destination tray 21 is mounted to the top of linear actuator 23 and is moved horizontally by linear actuator 23. Linear actuators 22 and 23 act to move destination tray 21 in the X and Y directions, respectively (see FIG. 7). Destination tray 21 is also rotatably attached to the top of linear actuator 23.

Figure 8:
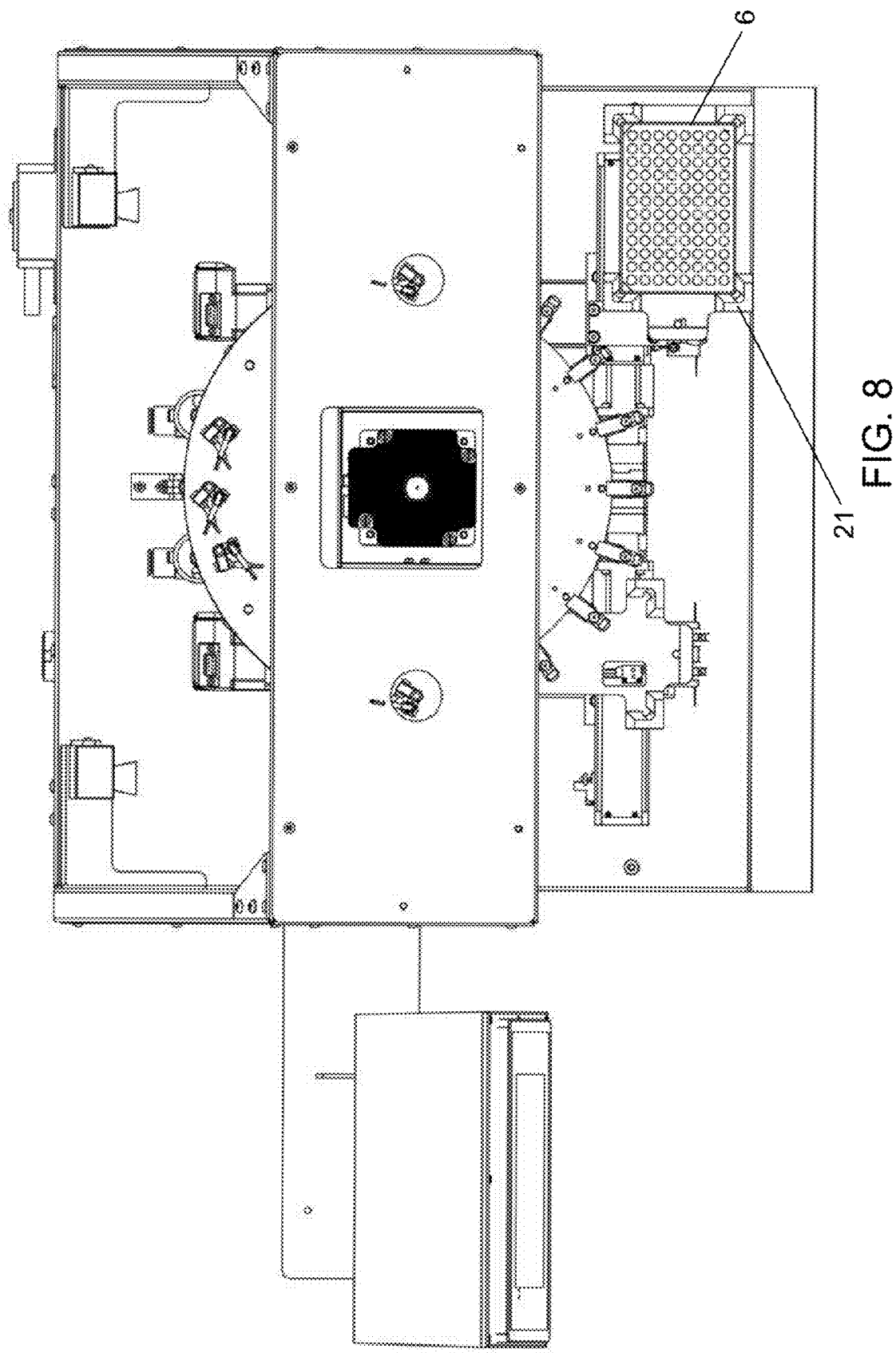

In FIG. 8, microwell plate 6 has been loaded onto destination tray 21. In a preferred embodiment, an automated device has placed microwell plate 6 onto source tray 21.

Figure 9:
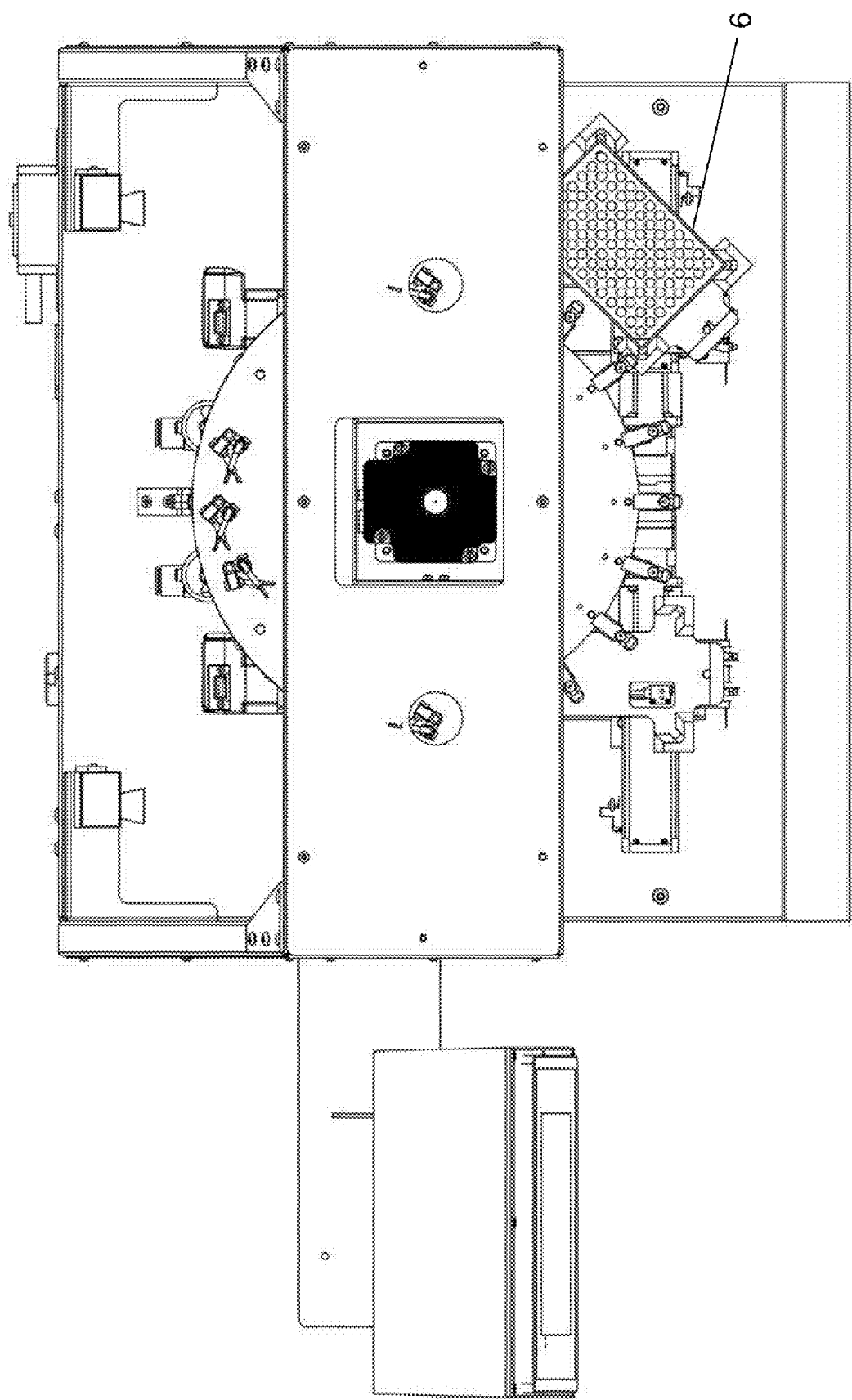

In FIG. 9, microwell plate 6 has been rotated counterclockwise approximately 45 degrees.

Figure 10:
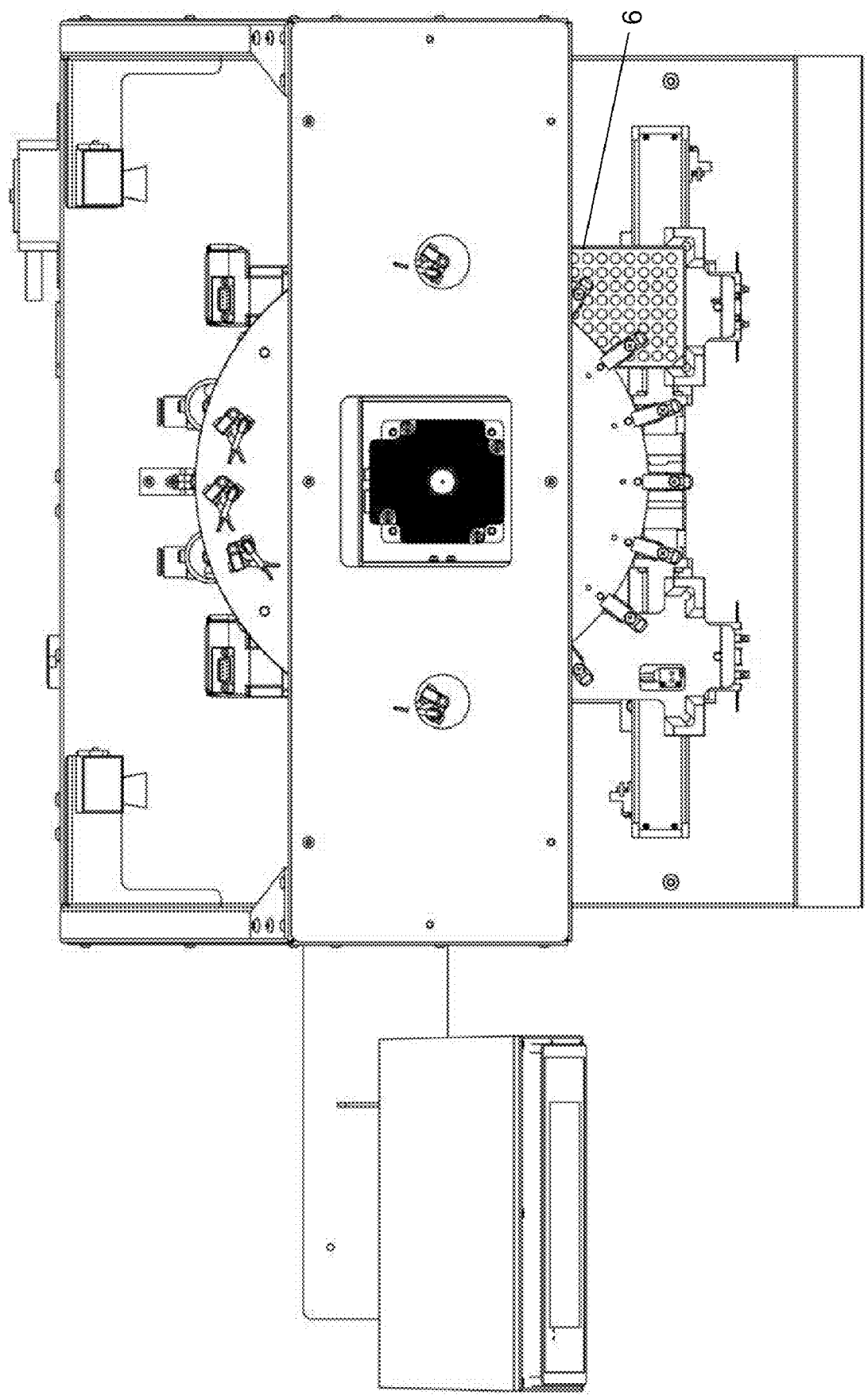

In FIG. 10, microwell plate 6 has been completely rotated 90 degrees counterclockwise from its position in FIG. 8.

Figure 11:
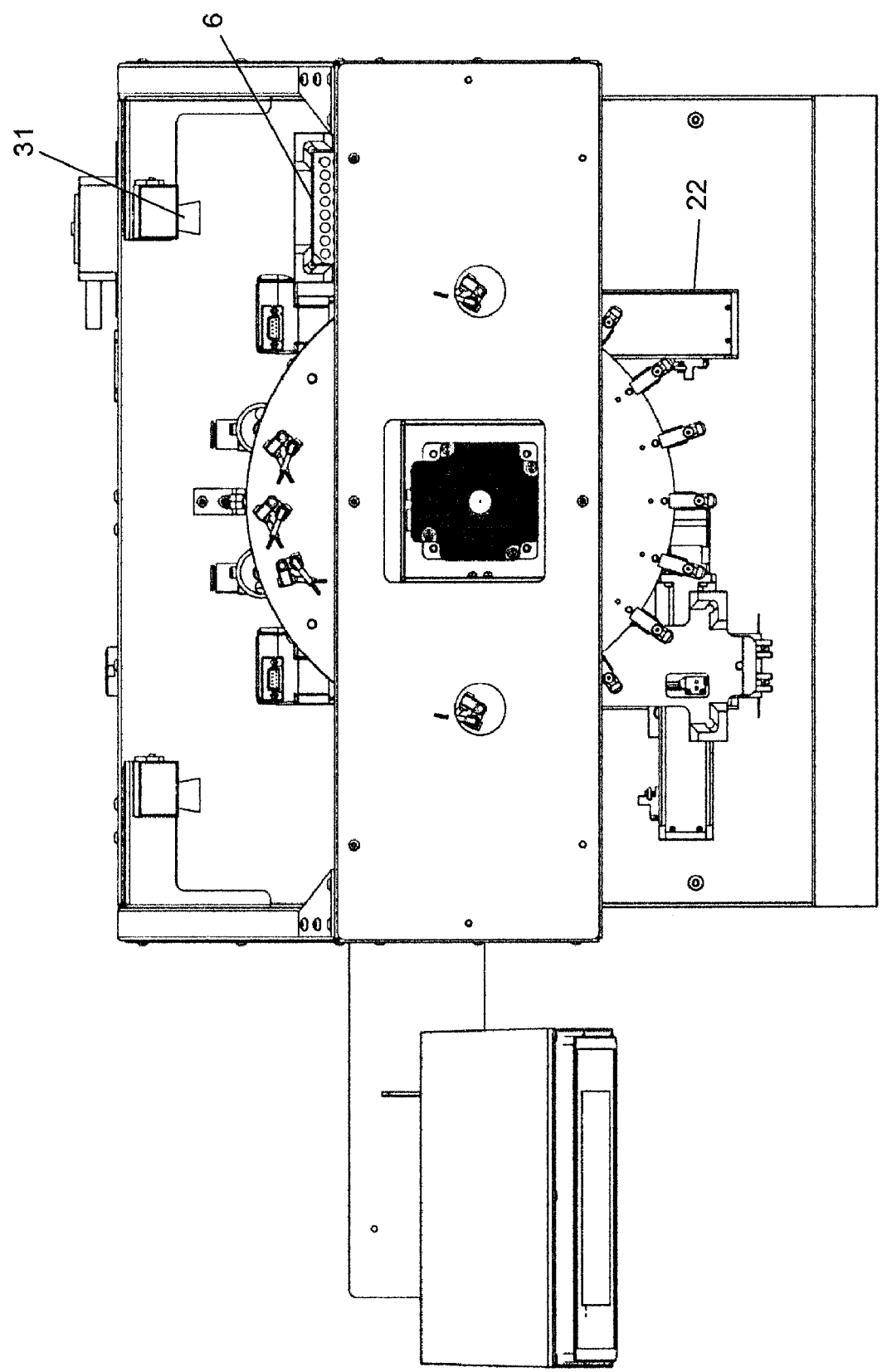

In FIG. 11, linear actuator 22 has moved microwell plate 6 towards barcode reader 31. Barcode reader 31 reads the barcode on microwell plate 6. This information is transferred to and recorded in computer 11.

Solution Transfer from Source Plate

Figure 12:
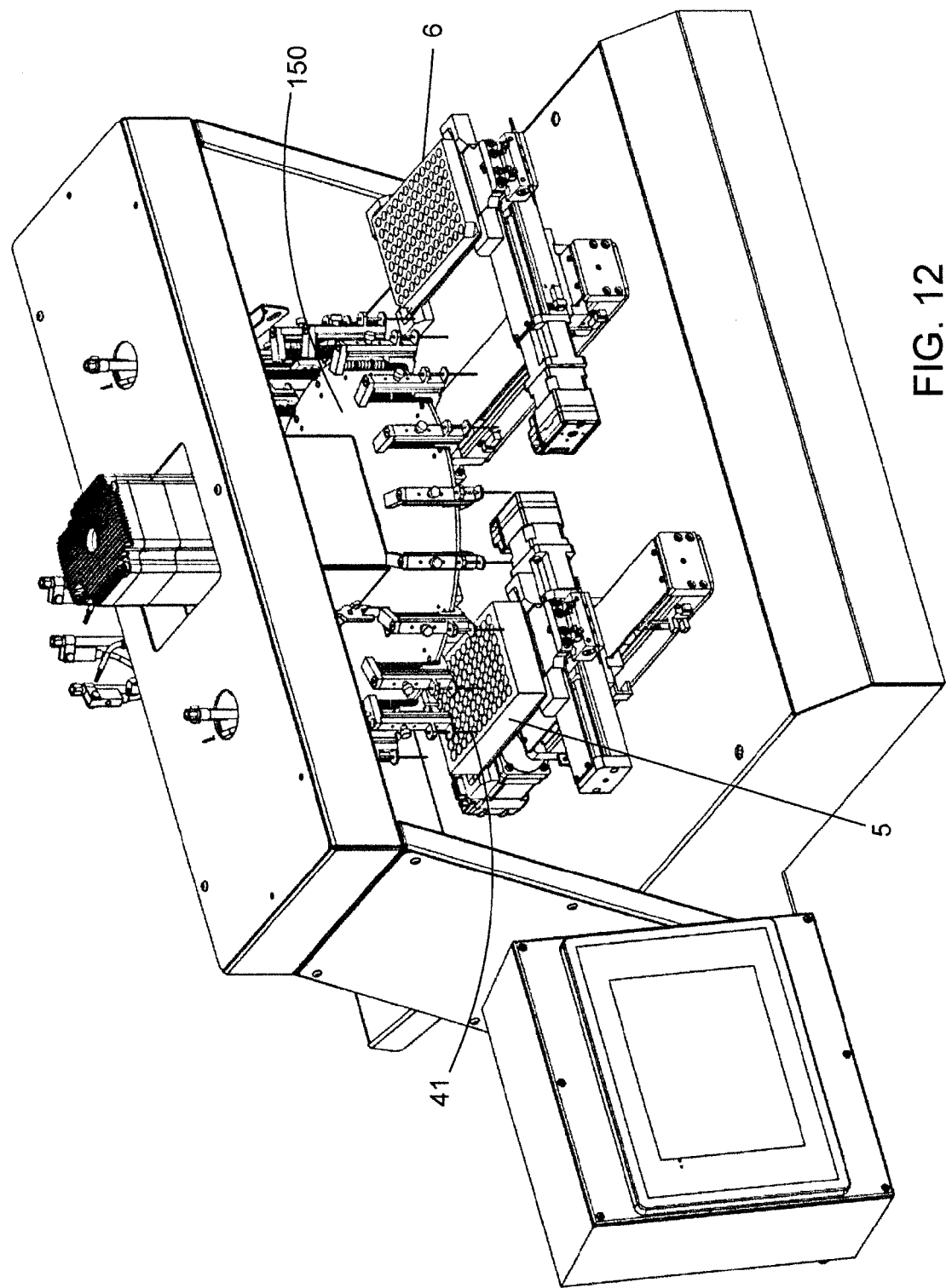

In a preferred embodiment, solution is transferred from microwell plate 5 and placed in microwell plate 6. FIG. 12 shows a detailed, perspective view of lowered pin 41 removing solution from a well of microwell plate 5. After solution has been picked up by pin 41, pin 41 will raise so that is above the top surface of microwell plate. Dial 150 will then rotate so that pin 41 is above a selected well of destination microwell plate 6. Solution is then deposited in a well of microwell plate 6.

To illustrate the operation of solution transfer machine 10 the "Plate Copy" mode is discussed. In the "Plate Copy" mode, solution is transferred from each well of a source plate to the same well of a similarly sized destination plate.

Figure 13:
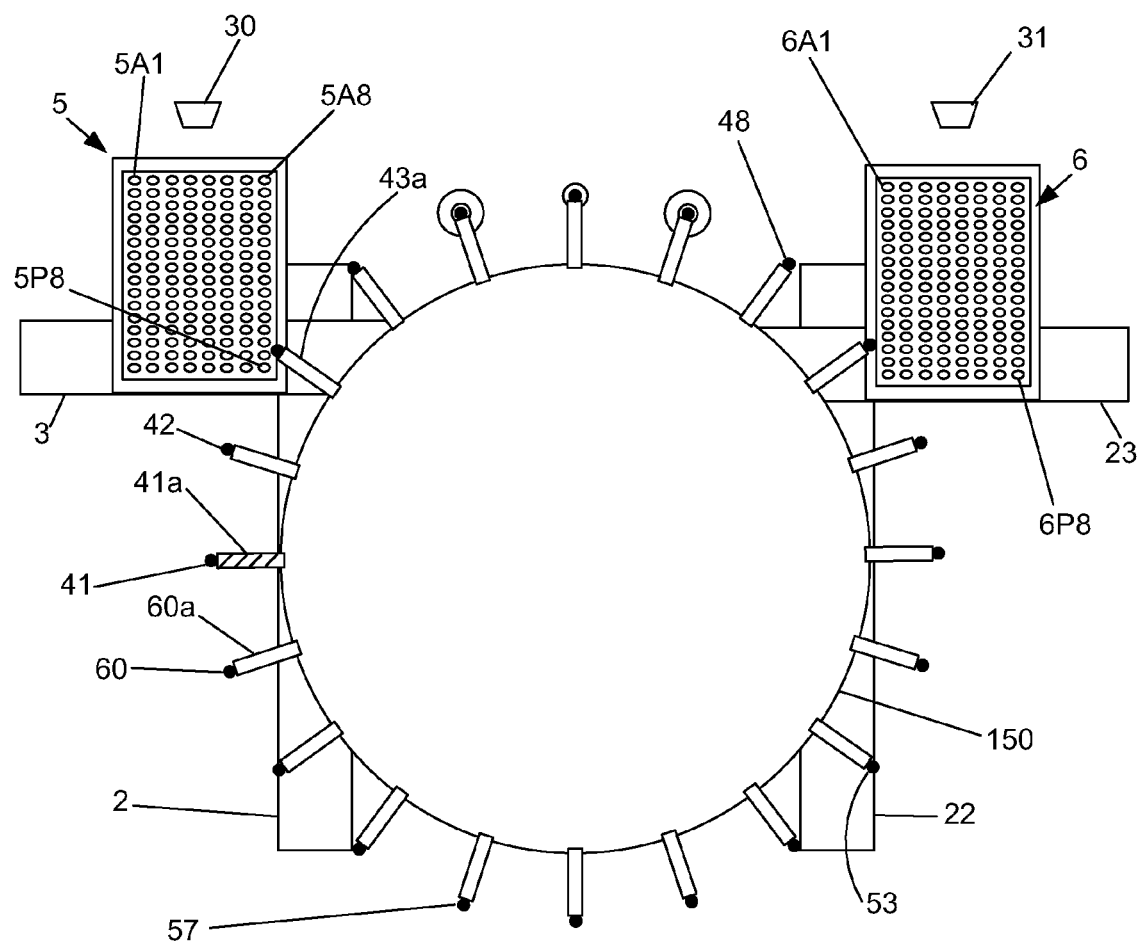

FIG. 13 shows a simplified view of microwell plate 5 and microwell plate 6 positioned in front of bar code readers 30 and 31. Pin assemblies 41a-60a are attached to dial 150 as shown. Linear actuators 2 and 3 function to position source microwell plate 5. Also, linear actuators 22 and 23 function to position destination microwell plate 6. Wells 5A1-5P8 for microwell plate 5 are shown. Likewise, wells 6A1-6P8 for microwell plate 6 are shown.

Figure 13A:
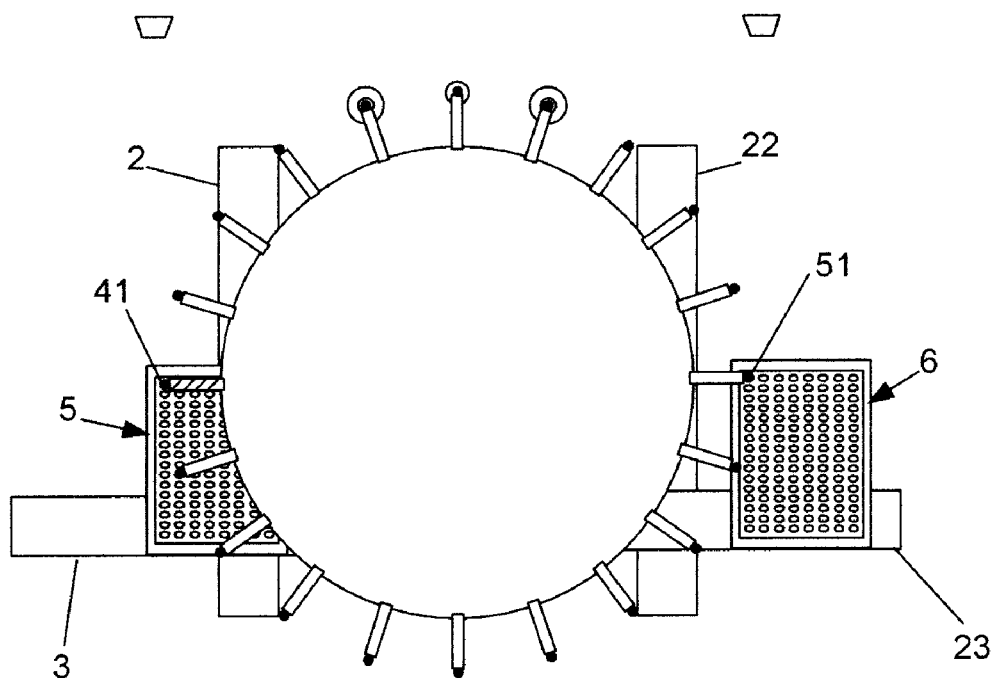

In FIG. 13a linear actuators 2 and 3 have moved microwell plate 5 under pin 41 so that well 5A1 is directly under pin 41. Also, linear actuators 22 and 23 have moved microwell plate 6 so that well 6A1 is directly under pin 51. Pin 41 has been lowered into well 5A1 and the pin has picked up the calibrated volume of solution. Pin 41 has then been raised.

Figure 14:
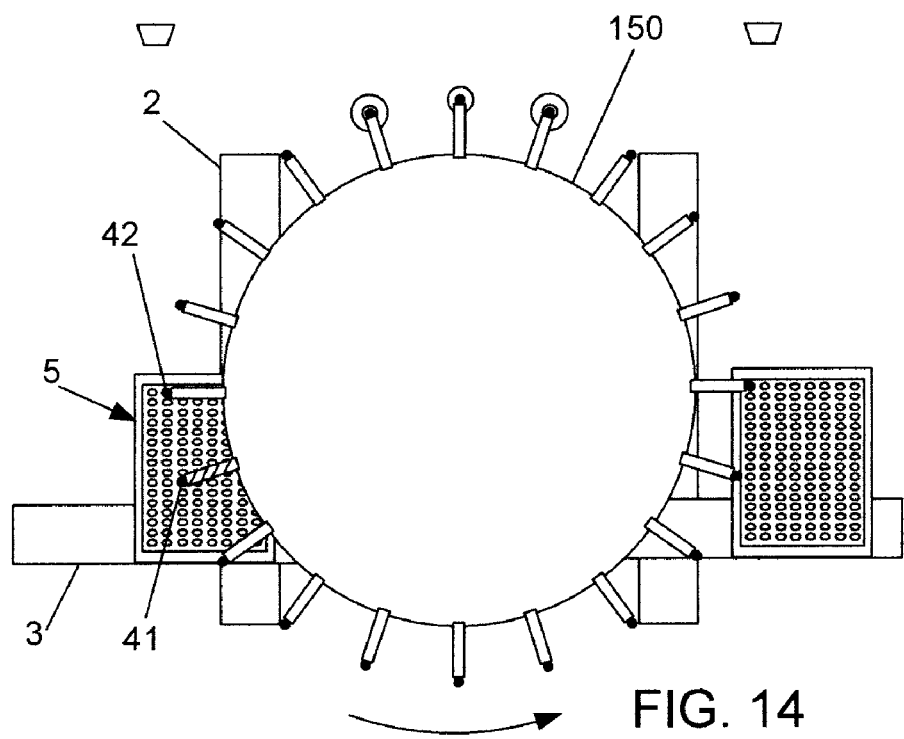

In FIG. 14 dial 150 has rotated counterclockwise so that pin 42 is in the position formally occupied by pin 41. Linear actuator 3 has moved microwell plate 5 to the left so that well 5A2 is under pin 42. Pin 42 has been lowered into well 5A2 and the pin has picked up the calibrated volume of solution. Pin 42 has then been raised.

Figure 15:
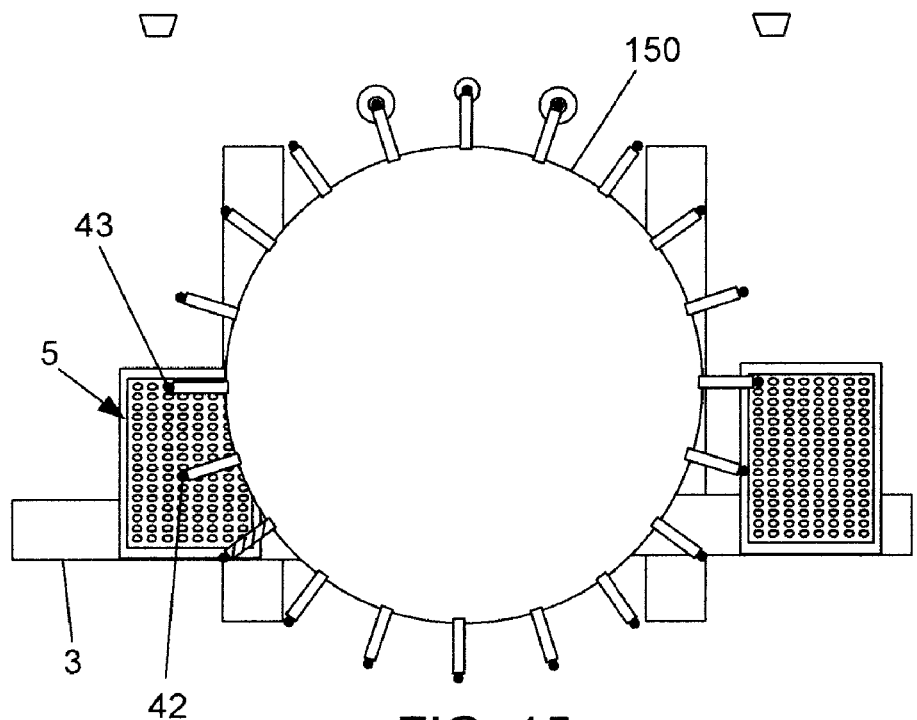

In FIG. 15 dial 150 has rotated counterclockwise so that pin 43 is in the position formally occupied by pin 42. Linear actuator 3 has moved microwell plate 5 to the left so that well 5A3 is under pin 43. Pin 43 has been lowered into well 5A3 and the pin has picked up the calibrated volume of solution. Pin 43 has then been raised.

Figure 16:
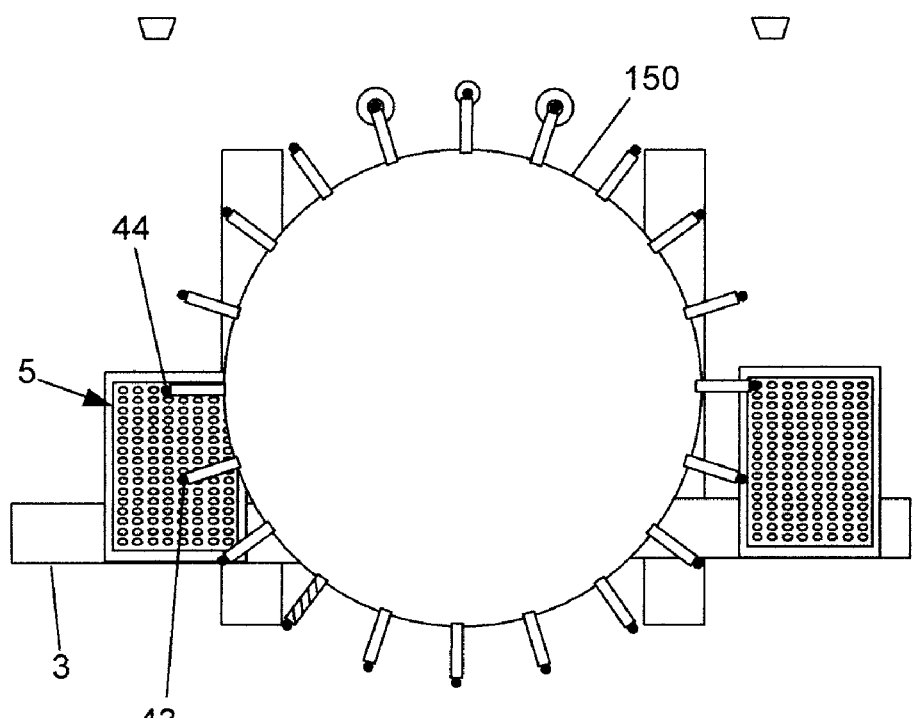
Figure 17:
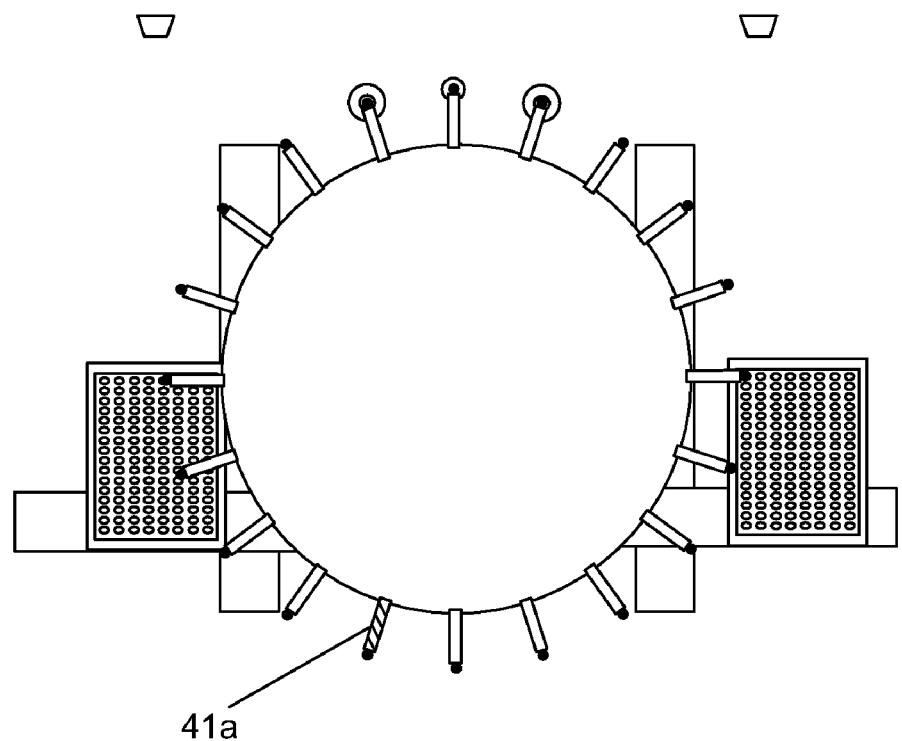
Figure 18:
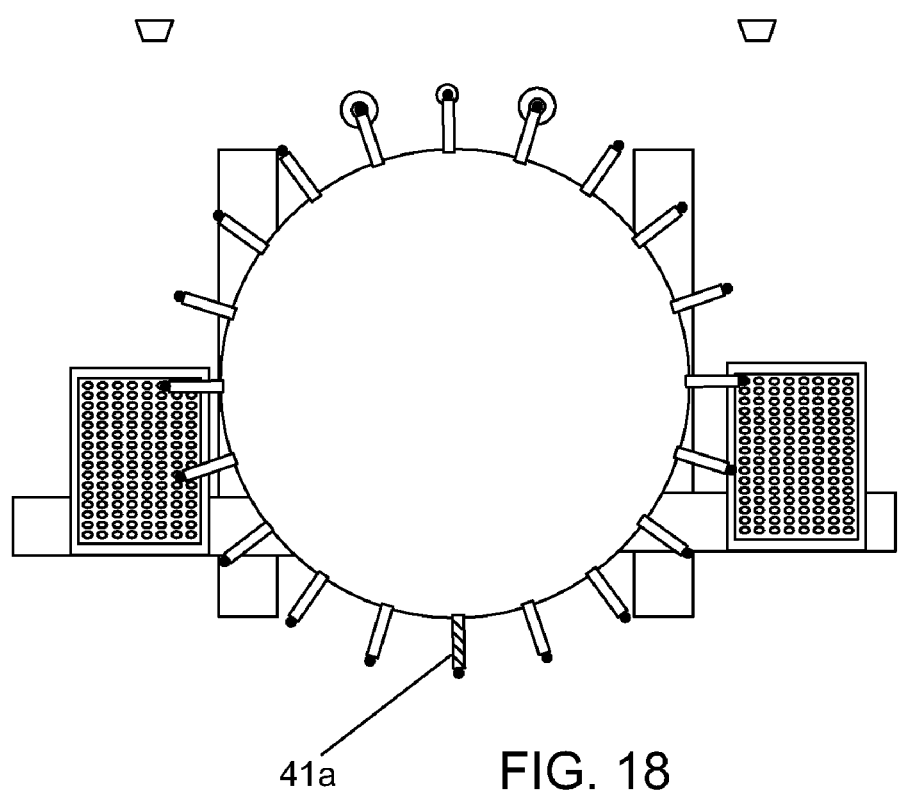
Figure 19:
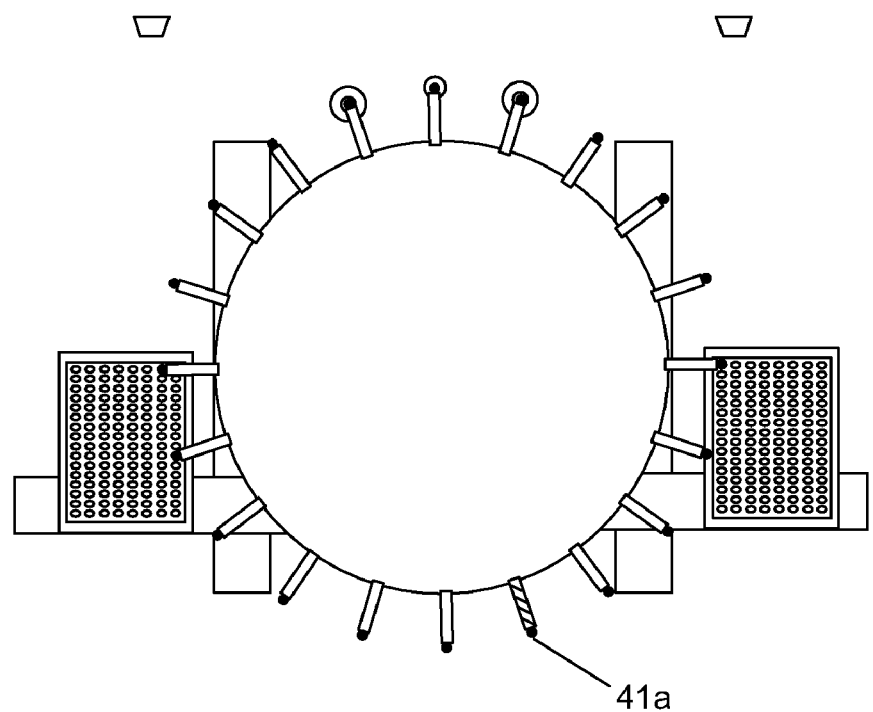
Figure 20:
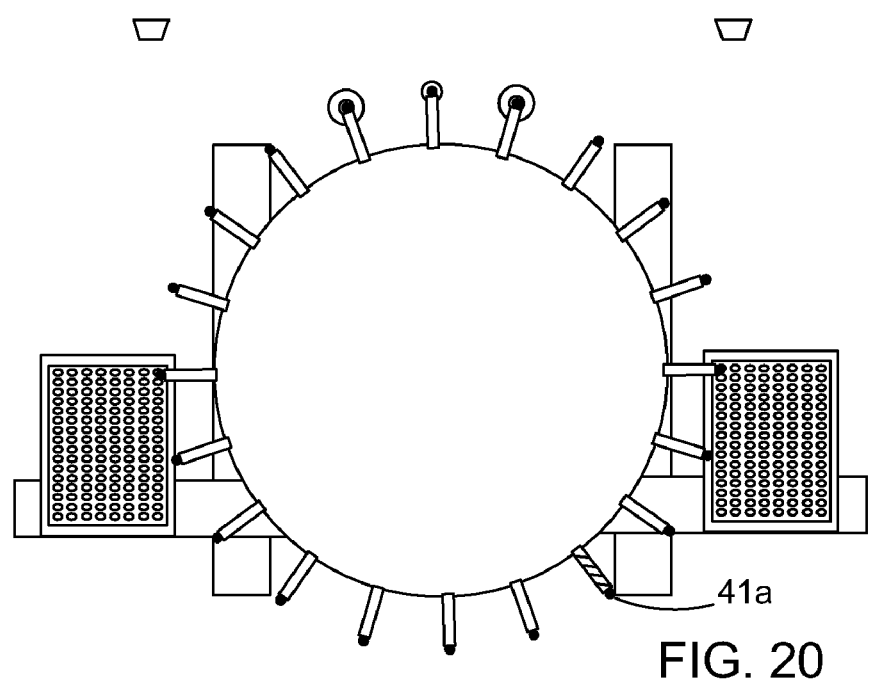

In FIG. 16 dial 150 has rotated counterclockwise so that pin 44 is in the position formally occupied by pin 43. Linear actuator 3 has moved microwell plate 5 to the left so that well 5A4 is under pin 44. Pin 44 has been lowered into well 5A4 and has picked up the calibrated volume of solution. Pin 44 has then been raised.

In this manner solution is removed from wells 5A5-5A8 (see FIGS. 13-20).

Figure 21:
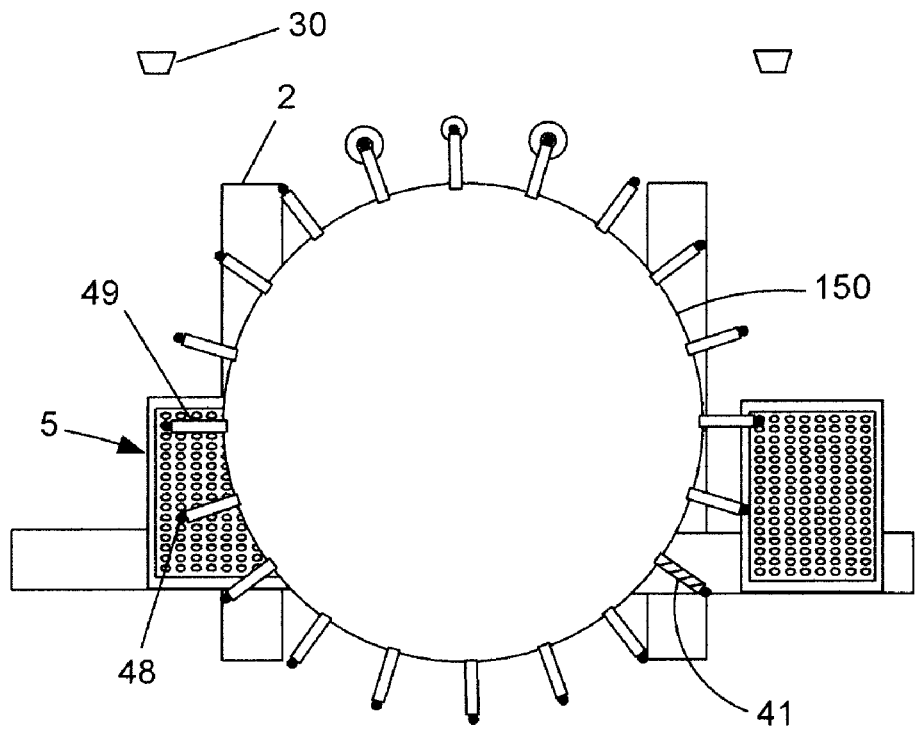

In FIG. 21 dial 150 has rotated counterclockwise so that pin 49 is in the position formally occupied by pin 48. Linear actuators 2 and 3 have moved microwell plate 5 so that well 5B1 is positioned under pin 49. Pin 49 has been lowered into well 5B1 and has picked up the calibrated volume of solution. Pin 49 has then been raised.

Figure 22:
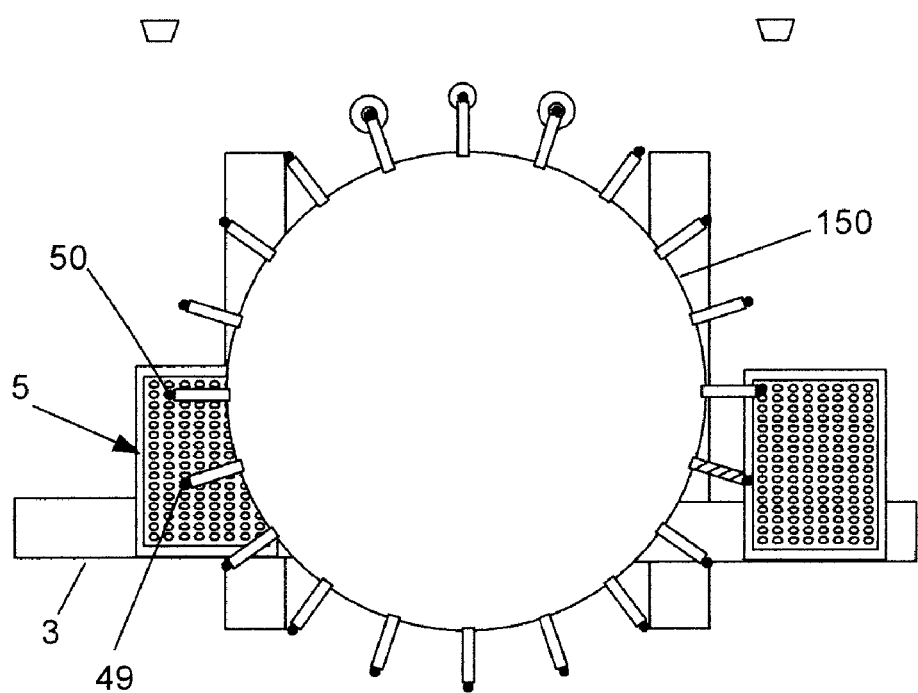

In FIG. 22 dial 150 has rotated counterclockwise so that pin 50 is in the position formally occupied by pin 49. Linear actuator 3 has moved microwell plate 5 to the left so that well 5B2 is under pin 50. Pin 50 has been lowered into well 5B2 and has picked up the calibrated volume of solution. Pin 50 has then been raised.

Figure 23:
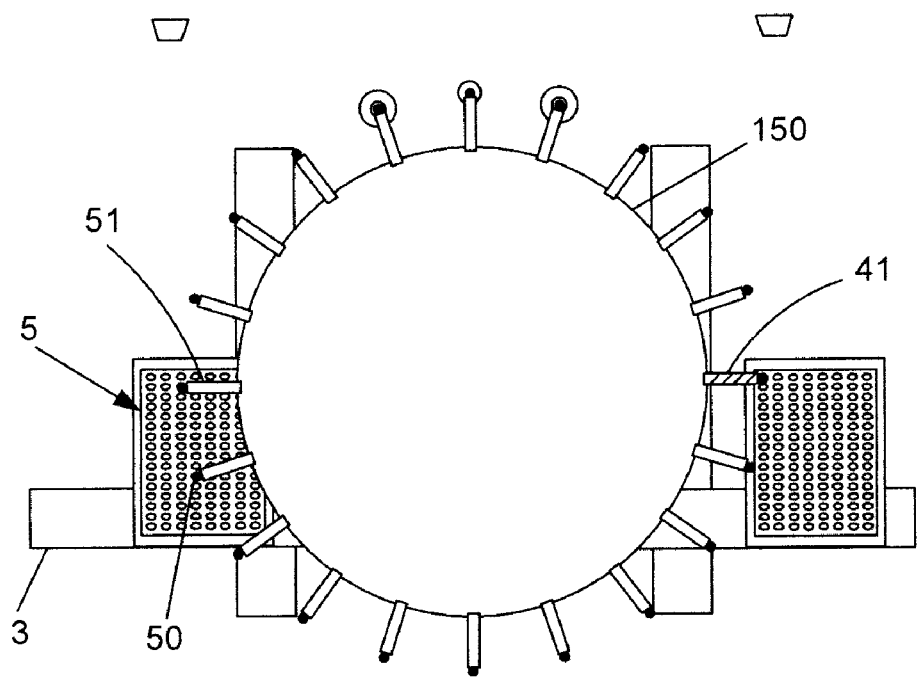

In FIG. 23 dial 150 has rotated counterclockwise so that pin 51 is in the position formally occupied by pin 50. Linear actuator 3 has moved microwell plate 5 to the left so that well 5B3 is under pin 51. Pin 51 has been lowered into well 5B3 and has picked up the calibrated volume of solution. Pin 51 has then been raised. Pin 41 has been lowered into well 6A1 of microwell plate 6 and has deposited its volume of solution. Pin 41 has then been raised.

Figure 24:
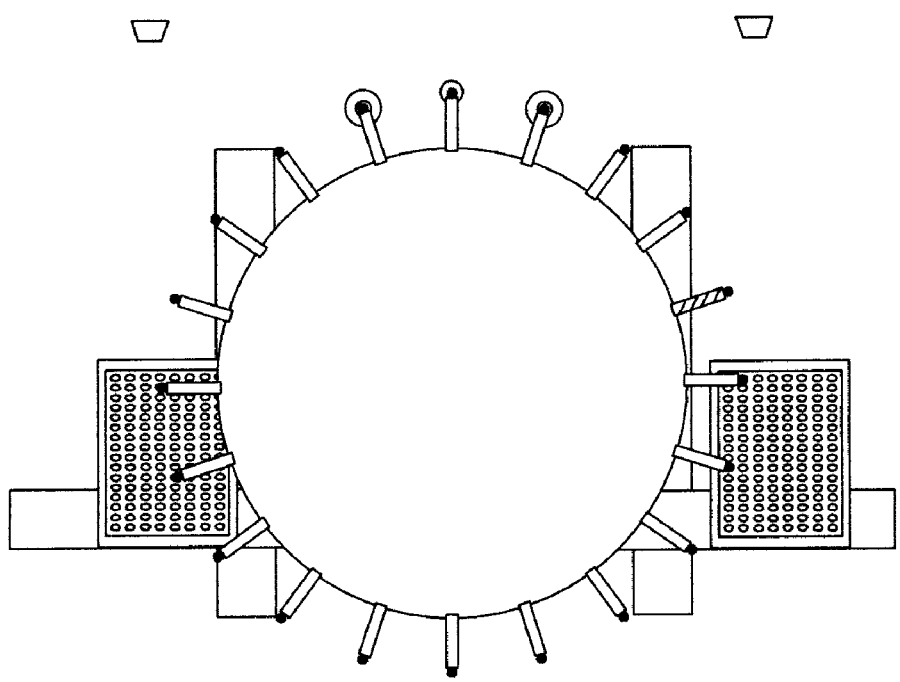
Figure 25:
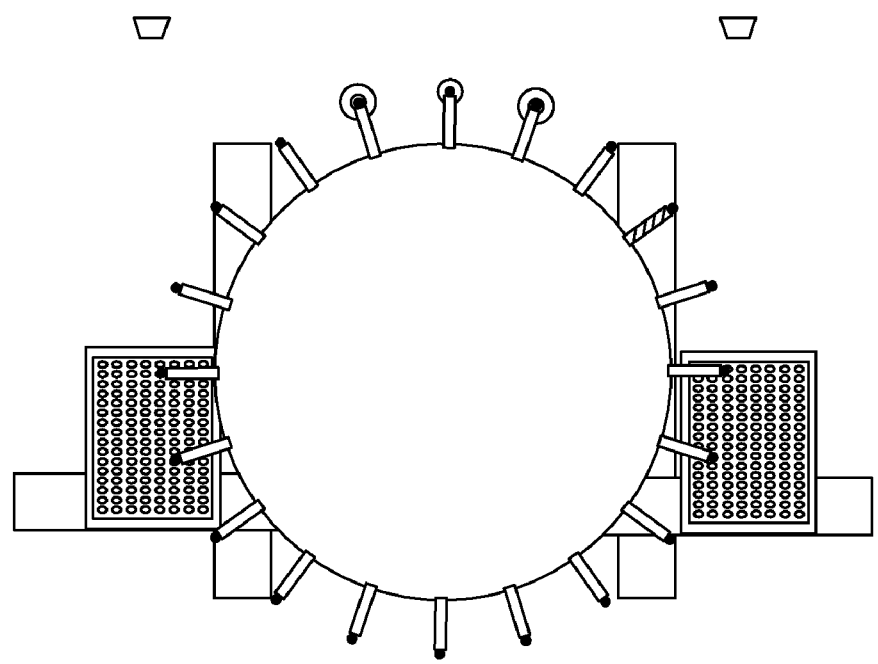
Figure 26:
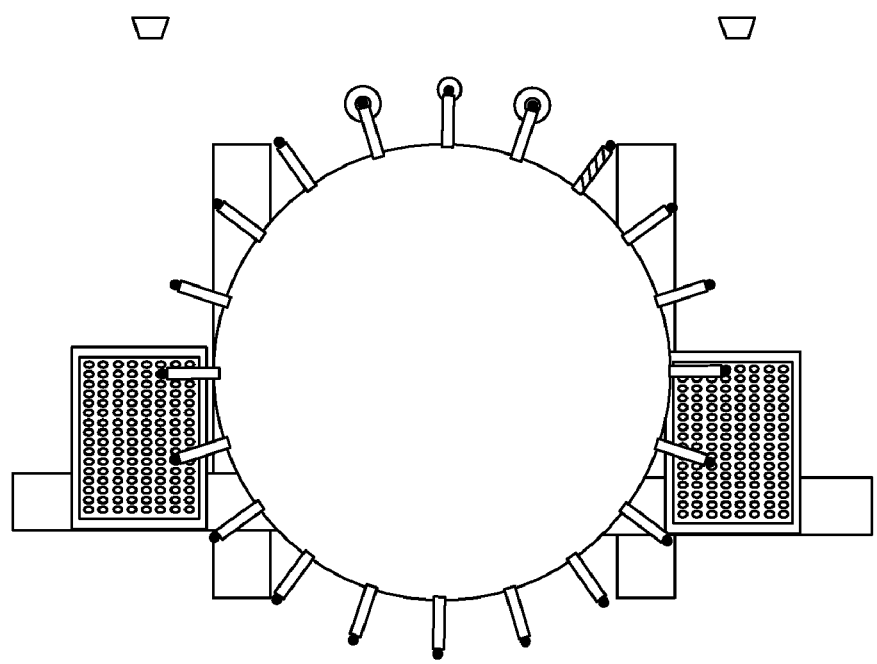

In this manner solution is removed from wells 5B4-5B6 and solution from wells 5A2-5A4 has been deposited into wells 6A2-6A4 (see FIGS. 24-26).

Figure 27:
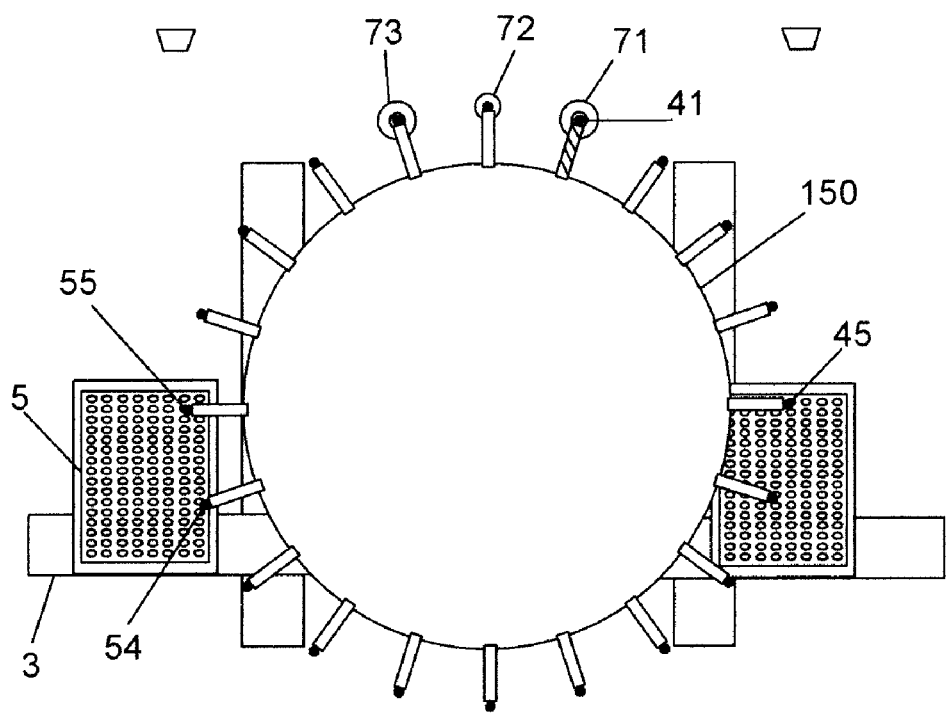
Figure 27B:
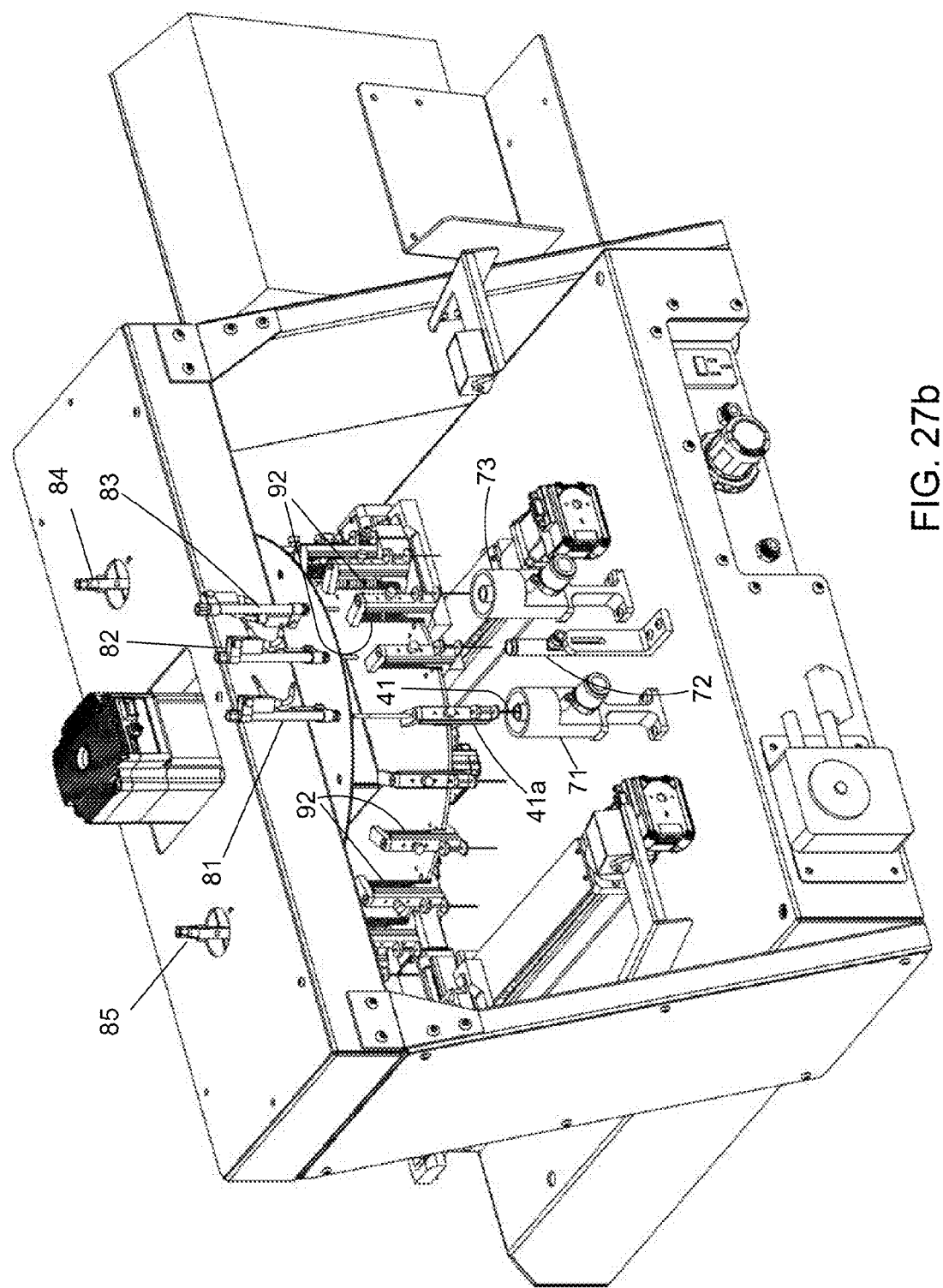

In FIG. 27 dial 150 has rotated counterclockwise so that pin 55 is in the position formally occupied by pin 54. Linear actuator 3 has moved microwell plate 5 to the left so that well 5B7 is under pin 55. Pin 55 has been lowered into well 5B7 and has picked up the calibrated volume of solution. Pin 55 has then been raised. Pin 45 has been lowered into well 6A5 of microwell plate 6 and has deposited its volume of solution. Pin 45 has then been raised. Pin 41 has been lowered into cleaning solution inside wash station 71 (see also FIG. 27b). Pin 41 has then been raised.

Figure 28:
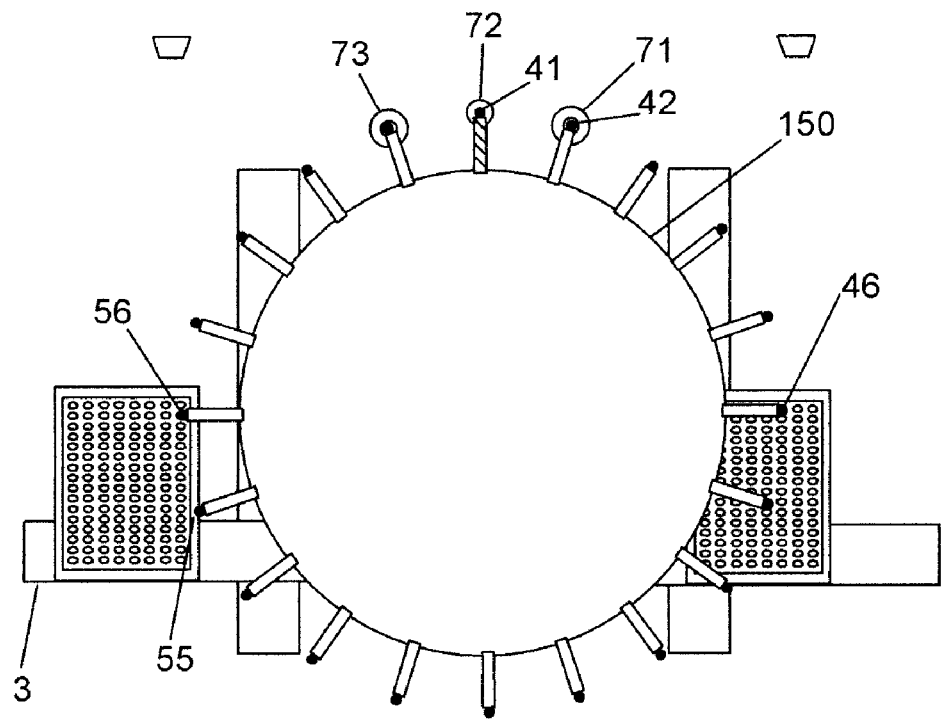
Figure 28B:
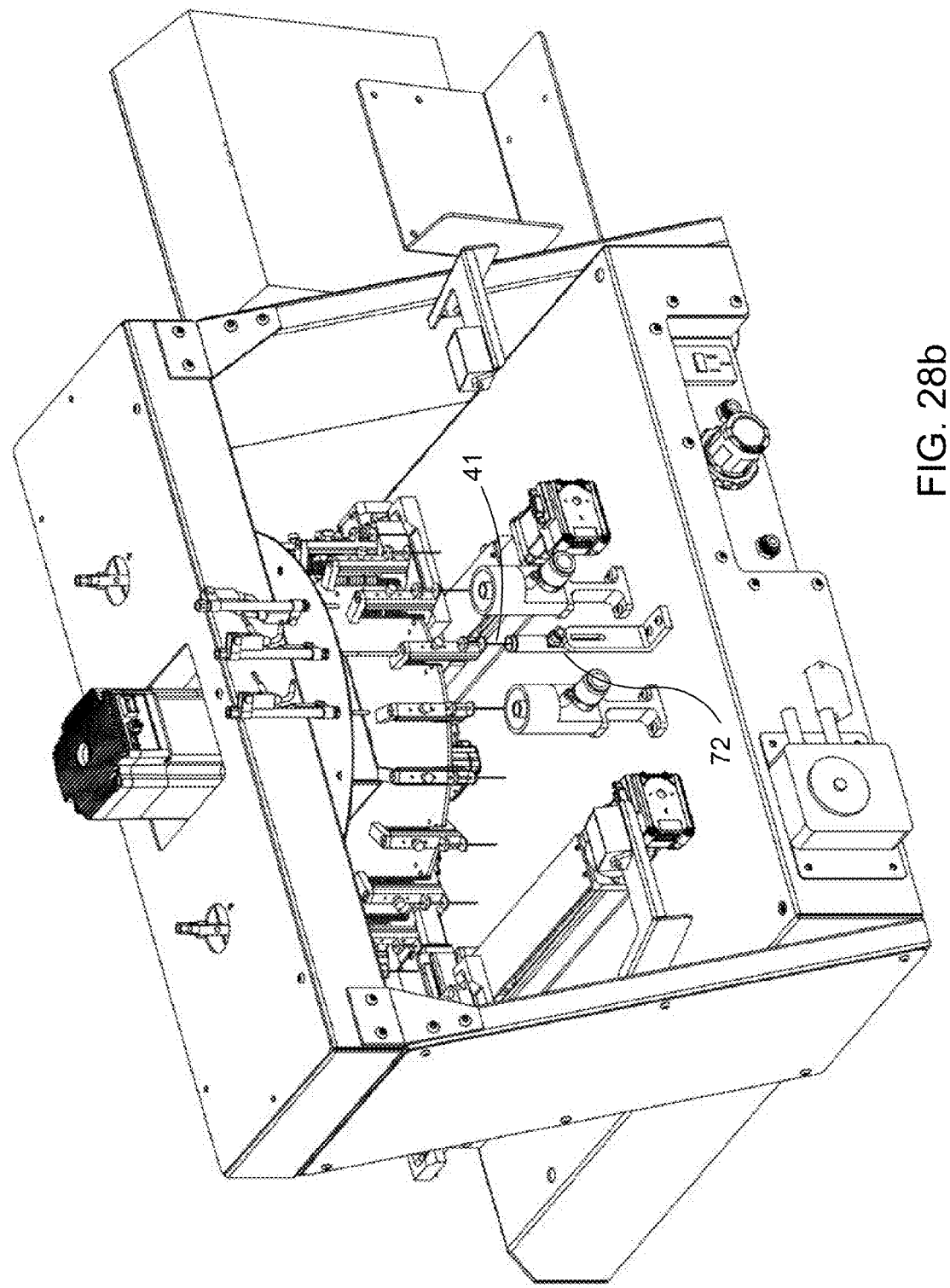

In FIG. 28 dial 150 has rotated counterclockwise so that pin 56 is in the position formally occupied by pin 55. Linear actuator 3 has moved microwell plate 5 to the left so that well 5B8 is under pin 56. Pin 56 has been lowered into well 5B8 and has picked up the calibrated volume of solution. Pin 56 has then been raised. Pin 46 has been lowered into well 6A6 of microwell plate 6 and has deposited its volume of solution. Pin 46 has then been raised. Pin 41 has been lowered into vacuum dryer 72 for drying. (FIG. 28b also shows pin 41 lowered into vacuum dryer 72.) Pin 41 has then been raised. Pin 42 has been lowered into cleaning solution inside wash station 71. Pin 42 has then been raised.

Figure 29:
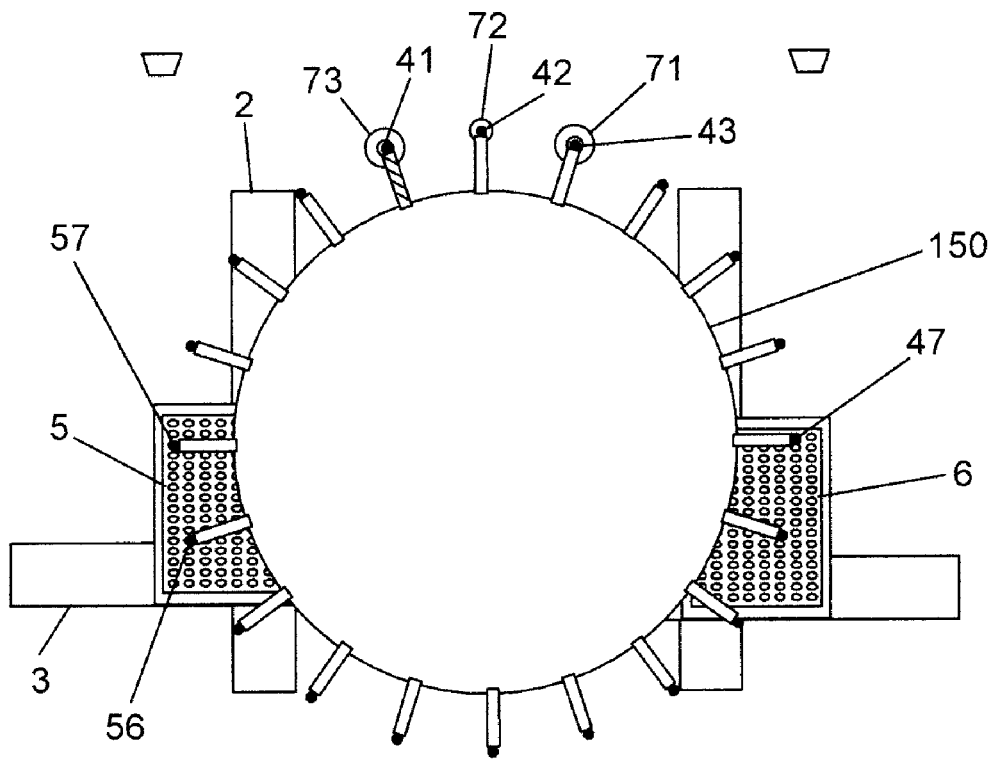

In FIG. 29 dial 150 has rotated counterclockwise so that pin 57 is in the position formally occupied by pin 56. Linear actuators 2 and 3 have moved microwell plate 5 so that well 5C1 is under pin 57. Pin 57 has been lowered into well 5C1 and has picked up the calibrated volume of solution. Pin 57 has then been raised. Pin 47 has been lowered into well 6A7 of microwell plate 6 and has deposited its volume of solution. Pin 47 has then been raised. Pin 41 has been lowered into alcohol rinse station 73 for further cleaning. Pin 41 has then been raised. Pin 42 has been lowered into vacuum dryer 72 for drying. Pin 42 has then been raised. Pin 43 has been lowered into cleaning solution inside wash station 71. Pin 43 has then been raised.

Figure 30:
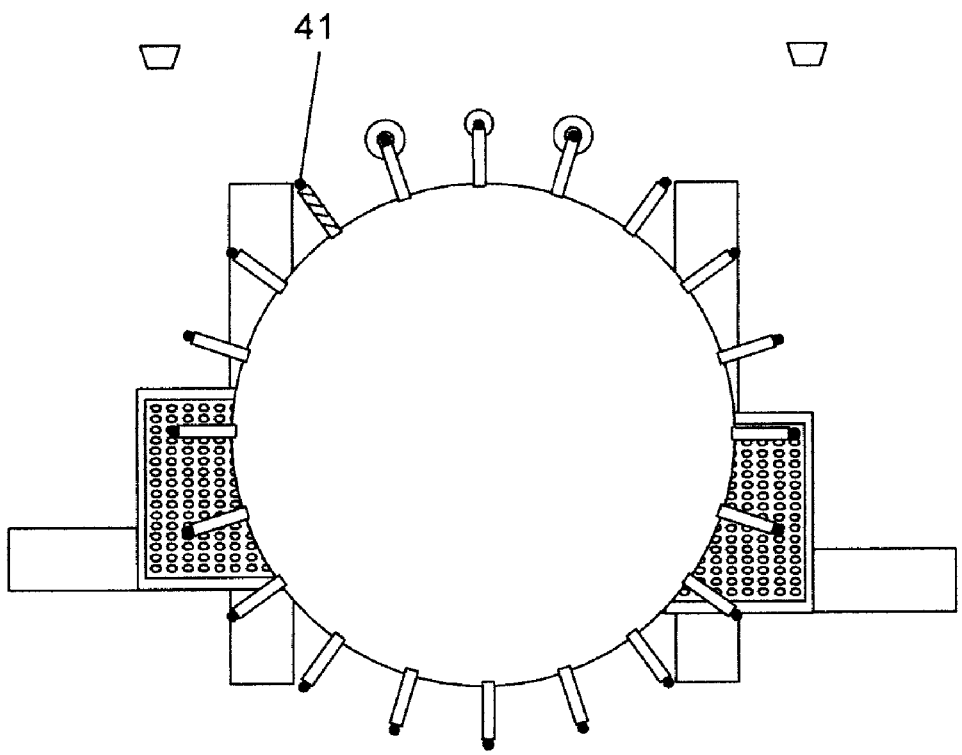

In FIG. 30 dial 150 has rotated one position counterclockwise so that pin 42 is in the position formally occupied by pin 41.

Figure 31:
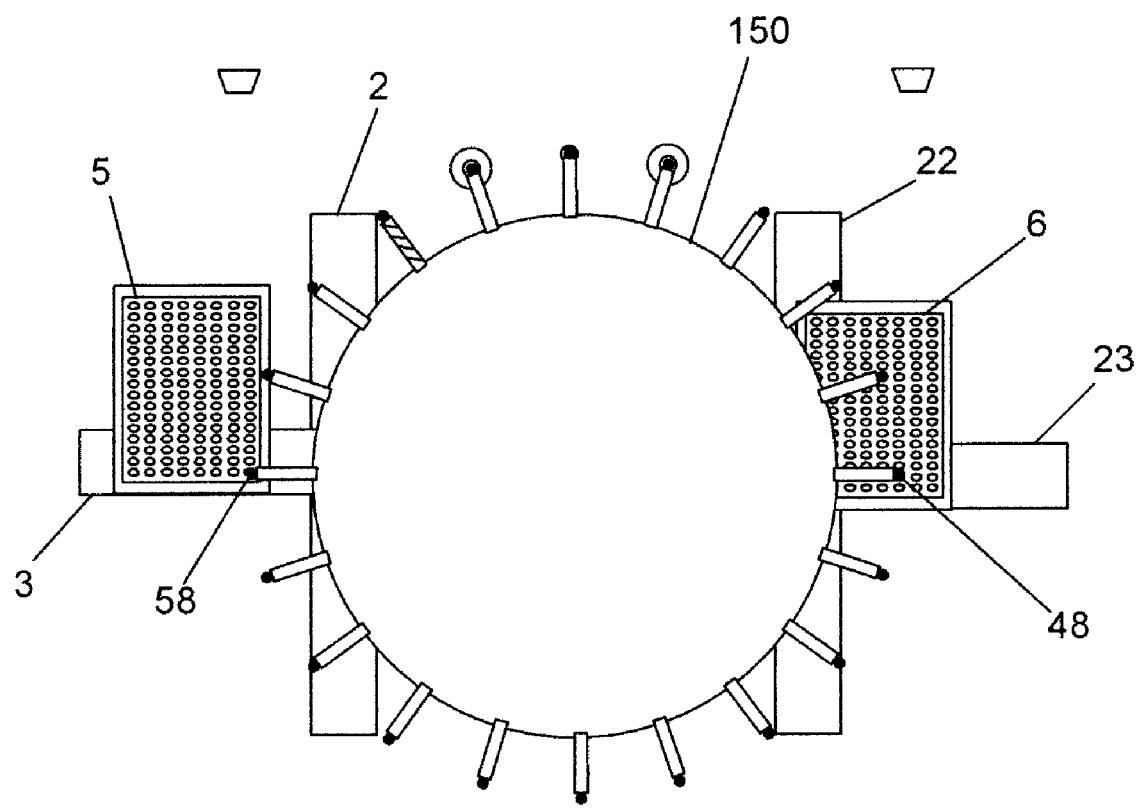

In this manner, the cycle continues until solution has been removed from each well of microwell plate 5 and transferred to microwell plate 6. For example, FIG. 31 shows pin 58 over well 5P8 of microwell plate 6. Pin 58 has been lowered into well 5P8 and has picked up the calibrated volume of solution. Pin 58 has then been raised. Pin 48 has been lowered into well 606 of microwell plate 6 and has deposited its volume of solution. Pin 48 has then been raised. From this point, dial 150 will continue to rotate and deposit solution into the remaining wells of microwell plate 6. After this has been completed, linear actuators 2 and 3 will position microwell plate 5 in the position shown in FIG. 3 so that microwell plate 5 can be removed. Likewise, linear actuators 22 and 23 will position microwell plate 6 at the position shown in FIG. 8 so that microwell plate 6 can be removed.

Plate Movement

As described above, solution transfer machine 10 (FIG. 1) transfers solution from wells of a source microwell plate to a destination microwell plate. The microwell plates can be loaded manually or by a robot into a tray. As shown in FIGS. 4-5 and FIGS. 9-10 solution transfer machine 10 is equipped with rotation stations to rotate source tray 1 and destination tray 21 in order to allow for easier loading and unloading. The rotation stations are each equipped with a pneumatic air cylinder that when actuated rotates the trays 90 degrees as controlled by computer 11. The trays are rotated to accept a plate in the orientation typically carried by a robot gripper. Also, the orientation allows for easy access by a human operator. Once the microwell plate is successfully loaded, the tray rotates back to the home position to begin the cherry picking process.

During the solution transfer process the microwell plates are moved to position the specified well to the pick location below the appropriate pin. This is accomplished by utilizing the two linear actuators.

Dial Movement

Figure 32:
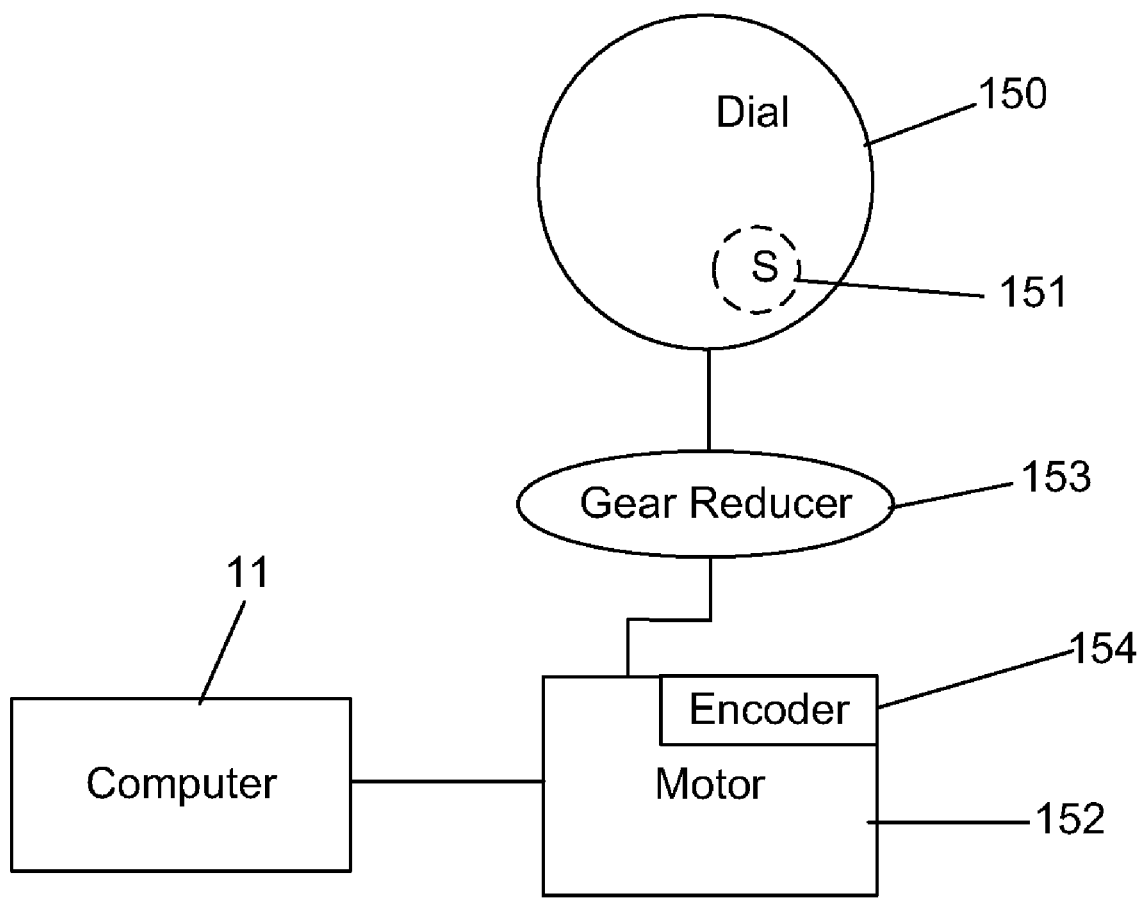
FIG. 32 shows computer control of the rotatable dial.

Twenty pins (41-60) are mounted to circular dial 150. Each pin is spaced at an equal angular increment around the circumference of dial 150. The motion of dial 150 is controlled by computer 11 (FIG. 32). Dial 150 is rotated by motor 152 through gear reducer 153. Motor 152 is equipped with encoder 154 which allows motor 152 to know its exact position. Home sensor 151 is mounted to dial 150 to tell the exact position of dial 150 in relation to motor 152. Dial 150 is indexed or rotated to the desired pin location. Once the pin is rotated to the location directly aligned with a plunger mechanism, the pin can be moved up and down to pick up or release solution, or to undergo a wash or dry process.

Pin Movement

As explained above, twenty slotted, floating pins are used in the system. The pin picks the calibrated volume of solution by extending into it. The pin releases solution by touching down in the destination location. Pins are moved up and down using a spring and plunger mechanism controlled by a linear actuator. For example, in FIG. 27b, pin assembly 41a is positioned beneath plunger 81. Plunger 81 has extended and has pushed pin assembly 41a downward so that pin 41 is pushed into wash station 71. When the plunger 81 retracts, spring 92 will push pin assembly 41a back up to its original position. As shown in FIG. 1, there are five plungers 81-85. Plunger 81 controls pin movement into wash station 71. Plunger 82 controls pin movement into vacuum dryer 72. Plunger 83 controls pin movement into alcohol rinse station 73. Plunger 84 controls pin movement into wells of source microwell plate 5. Plunger 85 controls pin movement into the wells of destination microwell plate 6. The speed at which the plunger mechanism actuates is controlled to aid in the pickup and delivery of solution carried by the pin.

Barcode Reading

The machine allows two barcode readers 30 and 31 to be mounted for reading the barcode of the source and destination plates, respectively. The plates are positioned using linear stages to the location which allows a laser scanner to read the barcode on the plate. The barcode can also be read using a hand scanner, or it can be recorded manually.

Variable Volume Transfers

The machine is designed to perform variable volume solution transfer. This can be accomplished in several ways. In one manner, each pin is designed to pick a specific volume of solution. The volume transferred is then the volume picked by the pin doing the transfer. Also, in another manner the machine can be equipped with a combination of pins equipped to pick different volumes. For example, pin 41 can have a specific volume capacity chosen by the operator. Pin 42 can have a different volume capacity and pin 43 can have yet its own unique volume capacity. The operator can then customize the volume transferred by picking solution from the same well on plate 5 using pins 41, 42 and then 43. Pins 41, 42 and 43 will then deposit the solution in the same well on destination plate 6. The volume transferred will then be the sum of the volume of solution in pins 41, 42 and 43. Computer 11 (FIG. 1) can be programmed to control solution transfer machine 10 to transfer solution from the source plate to the destination plate in the manner desired by the operator.

Alternate Dispense Options

In addition, other methods can be employed to pick and dispense solution. For example, a multiple pin head can be used to transfer the desired volume of solution. Or, a programmable syringe can also be fitted to pick and dispense the desired volumes.

Jerking Motion of Destination Plate during Transfer

Figure 37:
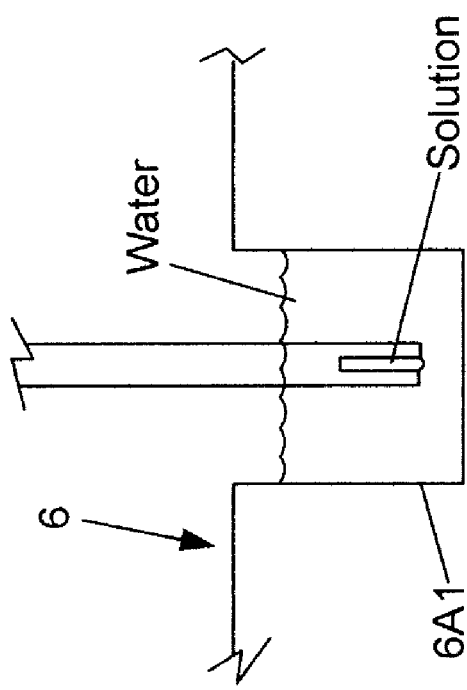
FIG. 37 shows a pin inserted into a well of the destination plate.

In a preferred embodiment, linear actuator 23 holding destination plate 6 conducts a quick back and forth jerking motion when the pin is inserted into the well of destination plate 6. The jerking motion assists in dislodging solution and assists in mixing the solution in the well. For example, FIG. 37 shows pin 41 inserted inside microwell 6A1 of destination microwell plate 6 (FIG. 1). While pin 41 is inserted inside microwell 6A1 linear actuator 23 moves side to side rapidly in a jerking motion to create agitation. The agitation creates turbulence in the water inside well 6A1 which causes solution on pin 41 to dislodge. The turbulence also causes proper mixing of the solution and the water inside the well.

Printing Arrays into the Wells of the Mircowell Plate

Figure 38:
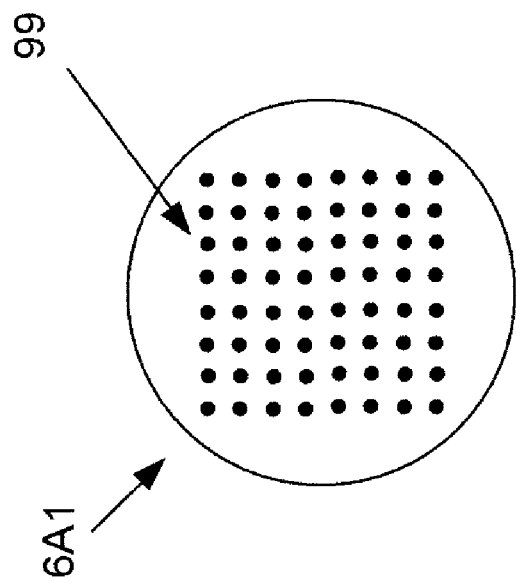
FIG. 38 shows a microarray printed onto a well of the destination plate.

FIG. 38 shows a top view of microwell 6A1 of destination plate 6. In a preferred embodiment, computer 11 is programmed to control linear actuators 23 and 22 to position destination plate 6 such that arrays can be printed into the bottom of each well of the destination plate. For example, FIG. 38 shows macroarray 99 printed into the bottom of microwell 6A1.

Data Storage

Computer 11 stores in its memory data that is reflective of the solution transfer process. For example, an operator can access computer 11 to determine the transfer status of the source and destination microwell plates. By referring to a specific barcode, the operator can ascertain the solution content of an individual well of a microwell plate.

Controller Operation

In a preferred embodiment, solution transfer machine 10 is controlled by a custom application written in a language supported by Microsoft Visual Studio for Microsoft.NET versions 2.0 and 3.5, (e.g. C# using Microsoft Visual Studio 2005). The application is hosted for either Windows Vista, Windows XP or Windows CE allowing the software to be run on either a regular windows XP laptop or on the Windows CE based computer with integrated touch panel offered as part of the hardware.

Figure 34:
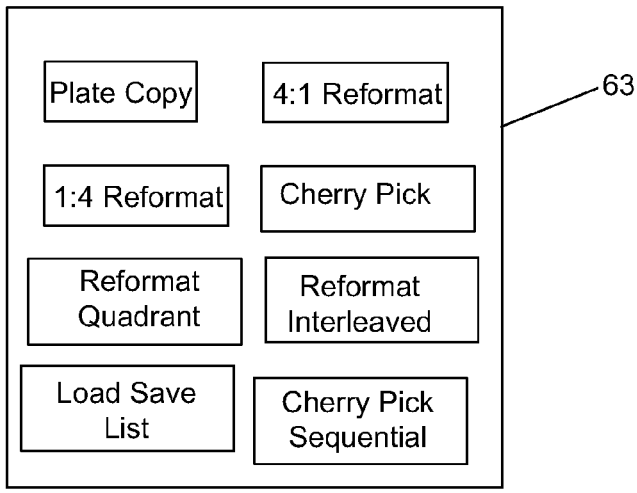
FIGS. 34-36 show a preferred computer screen interface.

For example, FIG. 34 shows a view of the screen 63 of computer 11. Computer 11 runs sequences of source to destination plate transfers and it supports several types of transfer. An operator controls the operation of solution transfer machine 10 by clicking on buttons shown on screen 63. Then, after selecting the transfer type the operator can input specifically the volume of solution that is to be transferred from each well.

To access the "Plate Copy" mode, the operator clicks on the "Plate Copy" button. In the "Plate Copy" mode, as the name suggests, transfers are made from each well of a source plate to the same well of a similarly sized destination plate (see example above).

The operator may also click on the "4:1 Reformat" mode or the "1:4 Reformat" mode to transfer solution between microwell plates of dissimilar size. In the "4:1 Reformat" mode four (4) 96 well source plates may be copied to a single 384 well destination plate. Likewise, in the "1:4 Reformat" mode, a single 384 well source plate may be copied to four (4) 96 well destination plates. In the "Reformat Quadrant" mode, the four 96 well plates are copied to or from the four 96 well quadrants of the 384 well plate. In the "Reformat Interleaved" mode, each distinct well from the four 96 well plates are copied to four adjacent wells in the 384 well plate, arranged in a square.

Figure 35:
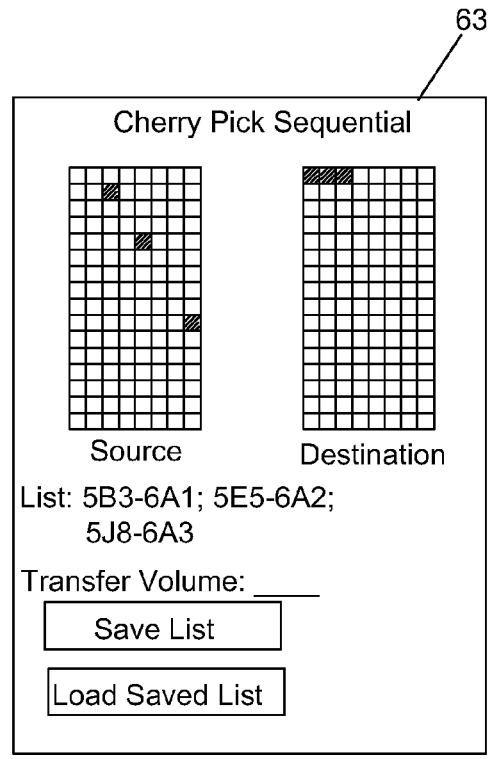
Figure 36:
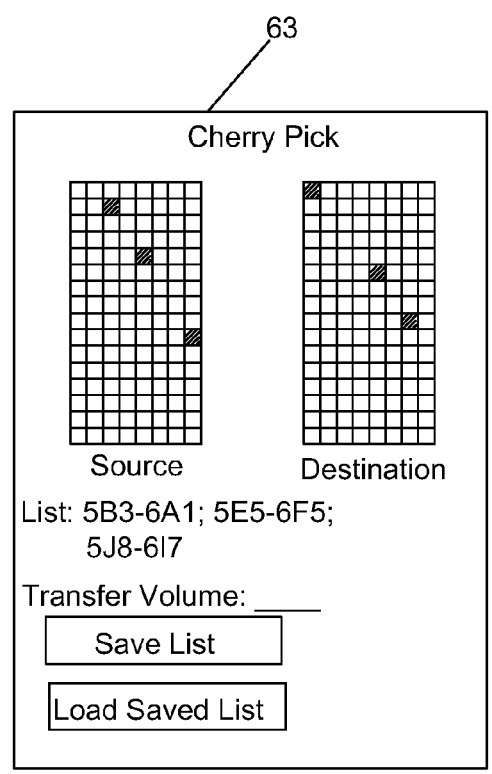

In the "Cherry Pick" mode, one or more wells from a number of source plates are copied to the destination plate; an input sequence usually contains a variable length list, where each item contains a source plate barcode, a source plate well number or id and an optional volume. Preferably, solution transfer machine 10 supports 2 variations of the "Cherry Pick" mode: 1) In the "Cherry Pick Sequential" mode, each source plate well is transferred to the next empty destination plate well and the output report file lists the contents of the destination plate (FIG. 35). In this mode, certain wells, rows or columns may be reserved for experiment control solutions and the sequential assignment flows around the reserved wells. An operator selects the wells from which solution will be taken by clicking on specific wells. For example, in FIG. 35 the operator has clicked on the shaded wells under for the "Source" plate. The program automatically sequentially will transfer the solution to the shaded wells on the "Destination" plate. 2) In the plate "Cherry Pick" mode, each sequence item is also specified the destination plate well (FIG. 36). For example, the operator chooses by clicking on specific wells for both the "Source" and the "Destination" plate. Then, after selecting the transfer type the operator can input specifically the volume of solution that is to be transferred from each well.

Also, the operator can save each transfer list that is created so that an identical transfer can be performed at a later time. The operator will run a saved transfer by clicking on the "Load Saved List" button.

Preferably, the hardware configuration provides network access and the machine comes configured with a collection of public shared folders or directories that are used to load jobs remotely and to retrieve completed job reports.

The input job file contains a high level description of the transfer required. A job preparation function of the application processes the input job, choosing the pin size and source plate pick order to optimize throughput. The resultant sequence is written to a pending sequence folder as a sequence file. The pending sequence folder acts as a queue to the sequence component of the software, which watches for changes in this directory. New sequences are displayed in an input sequence list on the application user interface. The job preparation module is designed to allow easy addition of new job input formats.

Figure 39:
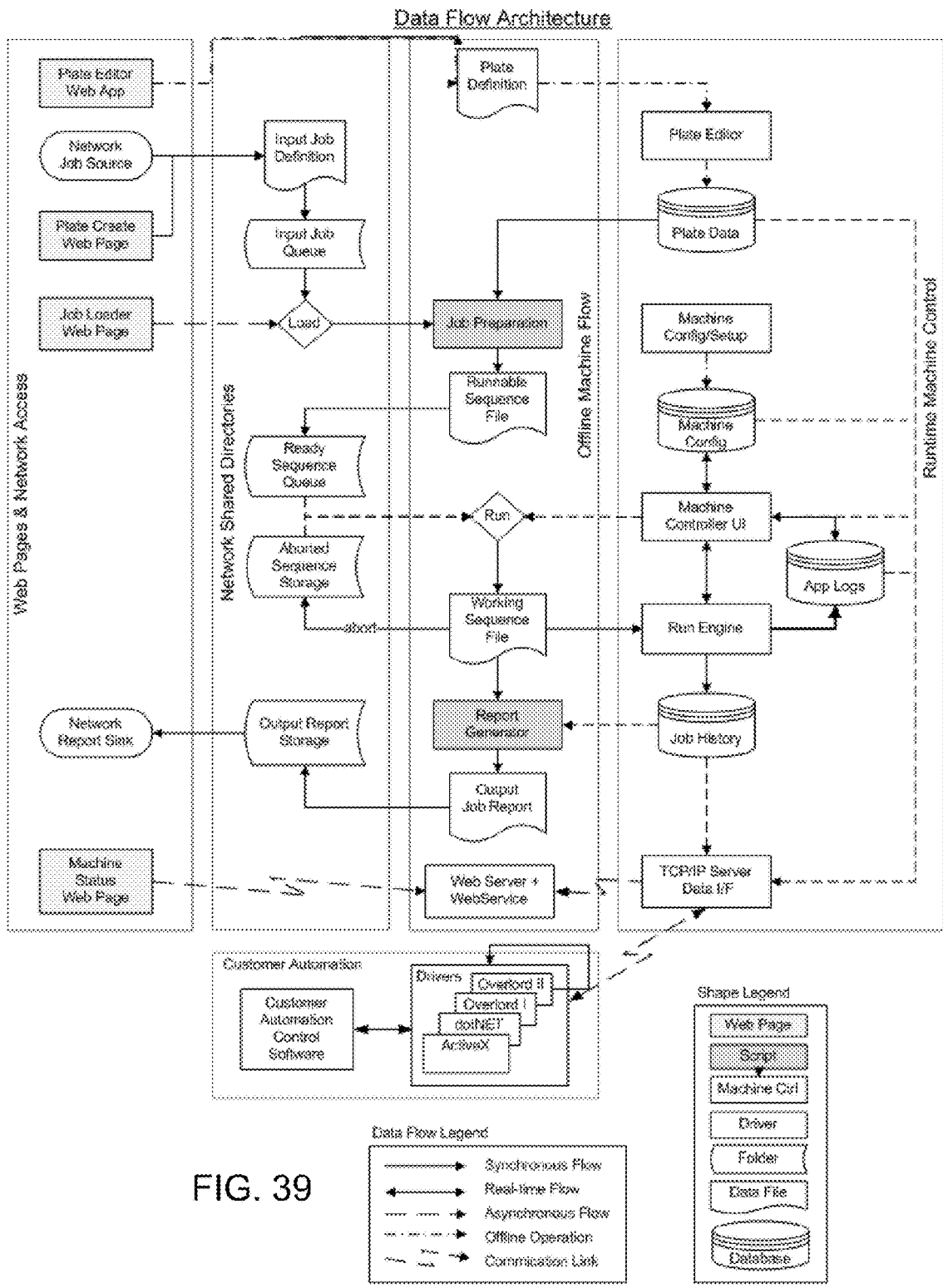
FIG. 39 shows a preferred data flow architecture.

A preferred data flow architecture is outlined in FIG. 39. In a preferred embodiment, the real-time control of solution transfer machine 10 is managed using software that allows the control logic to be modeled using diagrams drawn in Microsoft Visio according to the Unified Modeling Language (UML) "State Transition" diagram standard. These diagrams are imported by the state machine control, processed and converted to an XML file database. This database is loaded at runtime to handle the event driven control of the machine and provides a very efficient and reliable control system.

The control software uses an animation component. This component provides a very flexible and efficient graphical animation display that connects to the state machine control and the real-time event system to provide a real-time display of the rotary dial position, source and destination plate positions, current and processed wells and active pin and wash station solenoids.

The control application provides a plate editor and plate database allowing a user to define new plates and to teach new plate well positions quickly, simply and accurately using an animated graphical interface.

Extensive logging is provided using a Microsoft SQL Server Compact Edition database. The logs include an application log, a configuration log, a job history log, and an error log.

The control software supports a flexible automation interface allowing easy adaptation for robotic loading and unloading of plates.

The combination of a flexible TCP/IP interface to the control software allows remote monitoring and directly or, via a library of included drivers, supports integration with third party automation software.

Control Via Remote Access

The control application provides password protected remote access via publicly shared data folders or TCP/IP connection.

An additional software application also provides Web Site and Web Service remote access.

Public Shared Data Folders

A collection of data folders or directories on its control computer's hard drive are shared to allow remote job management.

A user can connect to the computer 11 across the company local area network, provided he has been given network access. Additionally, in a preferred embodiment, a user can connect to computer 11 from virtually any remote location via a computer network. For example, connectivity and control via the Internet is possible.

Using these shared folders, a user may queue jobs to be run by the computer 11 and retrieve completed job reports.

The control software uses a "FileWatcher" to monitor the input folder for added job files. These are read in automatically and validated. Good jobs are added to the input job queue of computer 11.

The new loaded jobs are processed by the computer 11 which verifies that the source and destination plate types are in the plates database. It then processes the job transfer list, chooses the pin sizes required for each transfer volume and orders the sequence to minimize the execution time. The result is a sequence file ready to be run by the sequencer of compute 11, written to a pending sequence queue.

Remote TCP/IP Connection

The control application includes a built-in TCP/IP server. This TCP/IP interface supports remote access from third party client applications.

The TCP/IP interface is designed primarily for remote monitoring, but, assuming the user has the required access level, it also allows some control over the machine mode and error handling and also editing of the input job queue.

Remote Monitoring
Overall machine mode and state
Individual hardware status
Current job information, including name, time, file name, progress and est. time of completion
Contents of input job queue, including scheduled completion time
Recent job history
Machine and job error history
Machine log contents
Machine operation, performance and reliability statistical data
Remote Editing
Input job queue
Clearing queue
Adding a job
Deleting a job
Changing job priority
Estimation of job execution time
Remote Control
Changing machine operational mode (give appropriate machine state)
Changing machine loading interface, between manual and robotic
Clearing of certain error conditions
Clearing of various logs
Reset of statistical data Remote Web Site and Web Service Access Using a local web server running on the control computer, this optional feature provides remote access via a web site or using a custom web service.

This optional software application connects to the running control application, via its TCP/IP interface.

These interfaces provide access to the same data as available through the TCP/IP interface describe above. In the case of the web site, the data is presented whenever appropriate using intuitive graphical or tabular formats.

Support is also provided on the web site for designing complex cherry picking jobs.

The web site's pages are updated in real-time using the latest AJAX and Web 2.0 technologies.

System Speed Optimization

Figure 33:
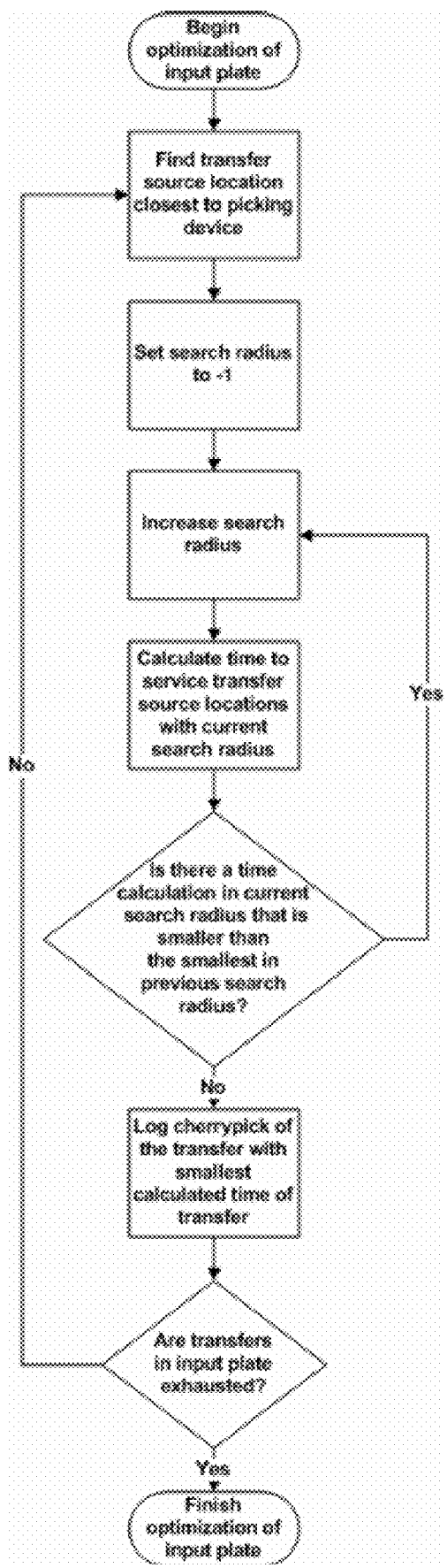
FIG. 33 shows a flow chart depicting a mathematical simulation of the system.

The software for the system is programmed to determine the most efficient sequence of picks in order to minimize the number of rotations of the dial to accomplish the input job. The optimization sequence treats the incoming job file generated by the user interface as a pool of transfer locations which must be serviced. The optimization is performed by producing a mathematical simulation of the system which is depicted in FIG. 33. Each input plate specified in the incoming job file is optimized independently of other input plates facilitating random input plate order. During the optimization, a sequence file is generated and, upon completion of the simulation, the sequence file is provided to the sequencer to proceed with the input job sequence.

Although the above-preferred embodiments have been described with specificity, persons skilled in this art will recognize that many changes to the specific embodiments disclosed above could be made without departing from the spirit of the invention. Therefore, the attached claims and their legal equivalents should determine the scope of the invention.

What is claimed is:

1. An automated machine for transferring solution from a source microwell plate to a destination microwell plate, comprising:
   A) a plurality of pins for transferring solution,
   B) a first actuator device for positioning said source microwell plate at a solution removal position accessible by each of said plurality of pins where solution is removed from said source microwell plate,
   C) a second actuator device for positioning said destination microwell plate at a solution transfer position accessible by each of said plurality of pins where solution is transferred to said destination microwell plate,
   D) a pin cleaning position accessible by each of said plurality of pins where each of said plurality of pins is cleaned,
   E) a circular dial rotatably connected to said automated machine, comprising:
      1. a plurality of pin assemblies connected to the outer circumference of said circular dial, wherein each of said plurality of pins is connected to one of said plurality of pin assemblies,
   F) a computer programmed to rotate said circular dial so that each of said plurality of pins is sequentially moved from said solution removal position to said solution transfer position to said pin cleaning position and back to said solution removal position.

2. The automated machine as in claim 1, wherein said first actuator device is at least one linear actuator for positioning said source microwell plate so that each well of said source microwell plate is positionable at said solution removal position so that said each well of said source microwell plate is accessible by each pin of said plurality of pins.

3. The automated machine as in claim 2, wherein said source microwell plate is rotatably attached to said at least one linear actuator.

4. The automated machine as in claim 2, wherein said at least one linear actuator is two linear actuators.

5. The automated machine as in claim 1, wherein said second actuator device is at least one linear actuator for positioning said destination microwell plate so that each well of said destination microwell plate is positionable at said solution transfer position so that said each well of said source microwell plate is accessible by each pin of said plurality of pins.

6. The automated machine as in claim 5, wherein said destination microwell plate is rotatably attached to said at least one linear actuator.

7. The automated machine as in claim 5, wherein said computer is programmed to control said at least one linear actuator to shake said destination microwell plate in a jerking motion to ensure solution is properly removed from each pin at said solution transfer position and to ensure said solution from each pin is properly mixed in said wells of said destination microwell plate.

8. The automated machine as in claim 5, wherein said at least one linear actuator is two linear actuators.

9. The automated machine as in claim 1, wherein said pin cleaning position comprises:
   A) a cleaning solution wash station,
   B) a vacuum drying station, and
   C) an alcohol rinse station,
   wherein said circular dial moves each pin of said plurality of pins from said cleaning solution wash station to said vacuum drying station to said alcohol rinse station.

10. The automated machine as in claim 1 comprising plungers positioned over said solution removal position, said solution transfer position, and said pin cleaning station for pushing said plurality of pins into said solution removal position, said solution transfer position, and said pin cleaning station.

11. The automated machine as in claim 1, wherein a microarray is printed onto at least one cell of said destination microwell plate.

12. The automated machine as in claim 1, wherein said computer is programmed to transfer solution from a source microwell plate to a destination microwell plate in accordance with a saved transfer list.

13. The automated machine as in claim 1, wherein said computer is programmed to accept a customized transfer list input by an operator.

14. The automated machine as in claim 1, wherein said computer is programmed to make said destination microwell plate a plate copy of said source microwell plate.

15. The automated machine as in claim 1, wherein said computer is controlled via a local area network.

16. The automated machine as in claim 1, wherein said computer is controlled remotely via the Internet.

17. The automated machine as in claim 1, wherein said computer is programmed to execute a saved transfer list and is programmed to accept a customized input list from an operator and execute said customized input list and save said customized input list for later execution.

18. The automated machine as in claim 1, wherein said plurality of pins is a plurality of pins of varying volume capacity for transferring variable volumes of solution.

19. The automated machine as in claim 18, wherein said computer is programmed to transfer variable volumes of solution.

* * * * *